United States Patent [19]

Klijanowicz et al.

[11] 4,423,126

[45] Dec. 27, 1983

[54] COLOR-FORMING CARBOXAMIDONAPHTHALENE DYE PRECURSOR AND CARBOXIMIDE DYE IN PHOTOGRAPHIC MATERIAL AND PROCESS

[75] Inventors: James E. Klijanowicz, Pittsford; Csaba A. Kovacs, Rochester, both of N.Y.

[73] Assignee: Eastman Kodak Company, Rochester, N.Y.

[21] Appl. No.: 382,546

[22] Filed: May 27, 1982

[51] Int. Cl.³ .................. G03C 7/00; G03C 1/10
[52] U.S. Cl. .................. 430/9; 430/17; 430/364; 430/375; 430/378; 430/380; 430/464; 430/467; 430/468; 430/483; 430/486; 430/542; 430/566; 430/955
[58] Field of Search .............. 430/9, 17, 224, 364, 430/375, 542, 955, 378, 380, 566, 467, 468, 464, 483, 486

[56] References Cited

U.S. PATENT DOCUMENTS

| | | | |
|---|---|---|---|
| 3,482,971 | 12/1969 | Bloom et al. | 96/3 |
| 3,620,731 | 11/1971 | Peisach | 96/3 |
| 3,938,995 | 2/1976 | Gompf et al. | 96/55 |
| 4,007,212 | 2/1977 | Curtis | 260/404.5 |
| 4,035,184 | 7/1977 | Faul et al. | 96/22 |
| 4,170,452 | 10/1979 | Grollier et al. | 8/10.2 |
| 4,368,246 | 1/1983 | Gabrielsen et al. | 430/955 |

FOREIGN PATENT DOCUMENTS 989862  5/1976  Canada .

OTHER PUBLICATIONS

*Research Disclosure,* Dec. 1978, Item No. 17643.

*Primary Examiner*—J. Travis Brown
*Attorney, Agent, or Firm*—Richard E. Knapp

[57] ABSTRACT

A new color-forming 4-(4'-secondary or tertiary-amino)anilino-1-carboxamidonaphthalene dye precursor in a photographic material and process enables formation of a dye image by means of cross-oxidation without the need for a coupling reaction. The color-forming 4-(4'-secondary or tertiary-amino)anilino-1-carboxamidonaphthalene dye precursor is useful in a photographic silver halide material for producing (i) a dye image, or (ii) a dye image and silver image. The exposed photographic material is processed to produce (a) a positive dye image, (b) a negative dye and negative silver image, (c) a negative dye image or (d) a positive dye image and a positive silver image. New naphthoquinoneimide dyes are also described.

57 Claims, No Drawings

COLOR-FORMING CARBOXAMIDONAPHTHALENE DYE PRECURSOR AND CARBOXIMIDE DYE IN PHOTOGRAPHIC MATERIAL AND PROCESS

FIELD OF THE INVENTION

This invention relates to a photographic material and process for producing images by means of photosensitive silver halide and a new color-forming 4-(4'-secondary or tertiary-amino)-anilino-1-carboxamidonaphthalene dye precursor.

DESCRIPTION OF THE STATE OF THE ART

Photographic materials for producing silver images and dye images are known. The dye image in such materials is generally produced by a coupling reaction in which a developing agent is oxidized upon development of photosensitive silver halide in the material, followed by reaction of the resulting oxidized form of the developing agent with a coupling agent to produce a dye image. It has been desirable to provide alternative means for producing a dye image, especially a dye image that enhances a silver image, other than by a coupling reaction. The formation of dye images according to the invention by means of a dye precursor does not involve a coupling reaction.

Production of reversal color images, also known as positive dye images, by developing a silver image in an imagewise exposed photographic material is also known. Such reversal color images and processes for producing such images are described in, for example, U.S. Pat. No. 4,035,184 and U.S. Pat. No. 3,938,995. These patents describe production of a dye image by means of a leuco dye comprising the reaction product of a color-forming coupler and an N,N-dialkyl-p-phenylenediamine. Neither of these patents relate to the formation of a dye image and silver image in which the dye is produced from a color-forming 4-(4'-secondary or tertiary-amino)-anilino-1-carboxamidonaphthalene dye precursor. The present invention also avoids the need for a coupling reaction to produce a dye described in these patents.

The term "photographic material" herein means photographic elements and photographic compositions. For instance, photographic material herein includes photographic elements and photographic compositions comprising photosensitive silver halide and a color-forming dye precursor according to the invention.

SUMMARY OF THE INVENTION

It has been found according to the invention that a stable dye image, especially a dye image that enhances a silver image, is produced by means of a photographic material comprising, in reactive association, in binder: (a) photosensitive silver halide, and (b) a color-forming dye precursor which is imagewise converted upon exposure and processing of the photographic material to a dye by cross-oxidation, preferably by means of a cross-oxidizing silver halide developing agent. The color-forming dye precursor according to the invention is a new color-forming 4-(4'-secondary or tertiary-amino)-anilino-1-carboxamidonaphthalene dye precursor.

It has also been found that a positive dye image is provided in a photographic material according to the invention by a process comprising (a) developing the exposed photographic material in an alkaline photographic developer in the absence of a cross-oxidizing silver halide developing agent; then, (b) fogging the resulting element, such as by uniformly exposing the resulting element to a flash exposure of light or, alternatively, a chemical fogging agent; followed by (c) developing the photographic element in an alkaline cross-oxidizing developer, such as a 3-pyrazolidone cross-oxidizing developer; and, then (d) bleaching and fixing the photographic material in a silver halide bleaching and fixing composition to produce a positive dye image in the photographic material. After step (a) and before step (b), optionally the photographic process for producing a positive dye image includes a stop bath treatment. This enables a desirable lowering of the pH of the development to a point at which development of a negative silver image stops quickly. This produces an improved dye image upon processing.

A negative dye image and a negative silver image are produced in an imagewise exposed photographic material comprising, in reactive association, in binder, (a) photosensitive siler halide, and (b) a color-forming 4-(4'-secondary or tertiary-amino)anilino-1-carboxamidonaphthalene dye precursor by developing the photographic material in an alkaline, cross-oxidizing, photographic silver halide developer composition, preferably such a composition comprising a 3-pyrazolidone silver halide developing agent. The negative dye image preferably enhances the negative silver image. This enables a lower concentration of silver in the photographic material before exposure than otherwise might be necessary to form a similar developed image from silver halide alone. When the negative, developed silver image is removed from the photographic material, such as by means of a bleaching and fixing composition, a negative dye image remains in the processed photographic material.

A positive dye image and a positive silver image are produced in an imagewise exposed photographic material according to the invention by means of direct-positive photographic silver halide. A process for producing a positive, dye image and a positive, silver image in an imagewise exposed photographic material comprising, in reactive association, in binder, (a) direct-positive photographic silver halide, and (b) a color-forming 4-(4'-secondary or tertiary-amino)anilino-1-carboxamidonaphthalene dye precursor comprises (A) developing the photographic element by means of an alkaline, cross-oxidizing photographic silver halide developing composition; then (B) fixing the resulting photographic element to produce a positive dye image and a positive silver image.

In each of the photographic materials and processes, the resulting naphthoquinoneimide dye in the image areas has good stability. The naphthoquinoneimide dye exhibits an increase in stability compared to a corresponding benzoquineimide dye. In naphthoquinoneimide dyes a ureido group provides increased stability compared to corresponding dyes comprising other carboxamido groups than a ureido group.

DETAILED DESCRIPTION OF THE INVENTION

Many 4-(4'secondary or tertiary-amino)-anilino-1-carboxamidonaphthalene compounds are useful color-forming dye precursors in photographic materials and processes according to the invention. Combinations of color-forming dye precursors are also useful, if desired. The color-forming 4-(4'-secondary or tertiaryamino)anilino-1-carboxamidonaphthalene dye precursor is selected to provide a naphthoquinoneimide dye image by means of a cross-oxidizing photographic silver halide developing agent after imagewise exposure.

One illustrative class of color-forming 4-(4'-secondary or tertiary-amino)anilino-1-carboxamidonaphthalene dye precursors is represented by the formula:

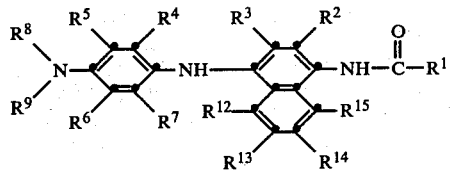

wherein

R¹ is alkyl, such as alkyl containing 1 to 25 carbon atoms, for example methyl, ethyl, propyl, butyl, decyl and eicosyl; cycloalkyl containing 5 to 8 carbon atoms, such as cyclohexyl and cyclopentyl; aryl, such as aryl containing 6 to 25 carbon atoms, for example, phenyl, tolyl and xylyl; alkoxy, such as alkoxy containing 1 to 25 carbon atoms, for example, methoxy, ethoxy, butoxy and decyloxy; aryloxy, such as aryloxy containing 6 to 25 carbon atoms, for example, phenoxy, tertiary-butylphenoxy and di-tertiary-amylphenoxy;

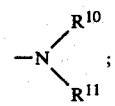

or a 5 or 6 member heterocyclic group, such as a 5 or 6 member heterocyclic group comprising nitrogen, oxygen, sulfur, carbon and hydrogen atoms, for example, morpholino, pyrrolino, pyridino, pyrimidino, oxazolino, thiazolino, and thiopheno groups;

$R^2$, $R^3$, $R^4$, $R^5$, $R^6$ and $R^7$ are individually hydrogen; alkyl, such as alkyl containing 1 to 25 carbon atoms, for example, methyl, ethyl, propyl, butyl, decyl and eicosyl; aryl, such as aryl containing 6 to 25 carbon atoms, for example, phenyl, tolyl and xylyl; alkoxy, such as alkoxy containing 1 to 25 carbon atoms, for example, methoxy, ethoxy, butoxy and decyloxy; arylsulfonyl ($Ar-SO_2-$), such as arylsulfonyl containing 6 to 25 carbon atoms, for example, phenylsulfonyl, naphthylsulfonyl, xylylsulfonyl and tolylsulfonyl; chlorine; bromine; carbamoyl; sulfamoyl; carboxy; sulfonamido; and carboxamido;

$R^8$ is hydrogen; alkyl, such as alkyl containing 1 to 25 carbon atoms, for example, methyl, ethyl, propyl, butyl, decyl, eicosyl, hydroxyethyl, methylsulfonamidoethyl and tolylsulfonamidopropyl; aryl, such as aryl containing 6 to 25 carbon atoms, for example phenyl, tolyl and xylyl; acyl, such as acyl containing 2 to 25 carbon atoms, for example acetyl, ethanoyl, heptanoyl, pivaloyl, undecanoyl, benzoyl and methylbenzoyl; carbamoyl, such as carbamoyl containing 2 to 25 carbon atoms, for example methylcarbamoyl, ethylcarbamoyl, decylcarbamoyl, and phenylcarbamoyl;

$R^9$ is alkyl, such as alkyl containing 1 to 25 carbon atoms, for example methyl, ethyl, propyl, butyl, decyl, eicosyl, hydroxyethyl, methylsulfonamidoethyl, tolylsulfonamidopropyl; aryl, such as aryl containing 6 to 25 carbon atoms, for example phenyl, tolyl and xylyl; alkylcarbonyl, such as alkylcarbonyl containing 2 to 25 carbon atoms, for example acetyl, ethanoyl, heptanoyl, pivaloyl and undecanoyl; carbamoyl, such as carbamoyl containing 2 to 25 carbon atoms, for example methylcarbamoyl, ethylcarbamoyl, decylcarbamoyl and phenylcarbamoyl; and arylcarbonyl, such as arylcarbonyl containing 7 to 25 carbon atoms, for example benzoyl and methylbenzoyl;

$R^{10}$ and $R^{11}$ are individually hydrogen; alkyl, such as alkyl containing 1 to 25 carbon atoms, for example, methyl, ethyl, propyl, butyl, decyl and eicosyl; aryl, such as aryl containing 6 to 25 carbon atoms, for example phenyl, tolyl and xylyl; a carbocyclic group, such as a 5 or 6 member carbocyclic group, for example, cyclohexyl; or, taken together represent the atoms, such as the oxygen, nitrogen, sulfur, carbon and hydrogen atoms, necessary to complete a 5 to 6 member heterocyclic ring, such as pyrrolino, pyridino, pyrimidino, thiazolino, oxazolino groups; and $R^{12}$, $R^{13}$, $R^{14}$ and $R^{15}$ are individually substituents that do not adversely affect desired photographic properties, for instance, hydrogen; alkyl, such as alkyl containing 1 to 25 carbon atoms, for example, methyl, ethyl, propyl, butyl, decyl and eicosyl; cyano (—CN); carboxamido; sulfonamido; sulfamoyl; chlorine; bromine; and alkoxy, such as alkoxy containing 1 to 25 carbon atoms, for example, methoxy, ethoxy, propoxy and eicosyloxy; and Ar is aryl, such as aryl containing 6 to 25 carbon atoms, for example phenyl, tolyl and xylyl.

The terms "alkyl" and "aryl" herein mean unsubstituted alkyl and unsubstituted aryl. The terms "alkyl" and "aryl" herein also mean substituted alkyl and substituted aryl wherein the alkyl and aryl are substituted by groups which do not adversely affect the dye precursors or the corresponding dyes according to the invention. Examples of suitable substituted alkyl groups include alkyl containing a sulfonamido group, such as $CH_3SO_2NH-$, a carboxamido group, an alkoxy group, such as methoxy or ethoxy, hydroxy, carboxyl (—COOH), an aryl group, such as a benzyl group, alkylcarbonyl, such as methylcarbonyl and ethylcarbonyl, arylcarbonyl, such as phenylcarbonyl, alkylamino, such as methylamino and ethylamino, arylamino, such as phenylamino. Another example of an alkyl group is

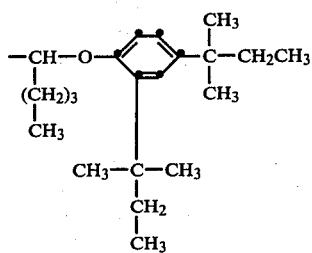

An alkyl group containing an aryl substituent is also known as an aralkyl group. Examples of suitable substituted aryl groups include phenyl containing an alkoxy group, such as methoxy and ethoxy, carboxyl, alkyl such as methyl, ethyl, propyl and butyl, and hydroxy. An especially useful substituted aryl group is an alkyl substituted aryl group, such as tolyl, 2,4,6-triisopropylphenyl and t-butylphenyl. An alkyl substituted aryl group is also known as an alkaryl group.

Particularly useful dye precursors and corresponding dyes in imaging materials and processes are those wherein $R^1$ is $NH-R^{10}$. This group forms a ureido group on the naphthalene dye nucleus. It enhances dye stability and increases the ease of dye formation.

An example of a class of color-forming compounds according to the invention is represented by the formula:

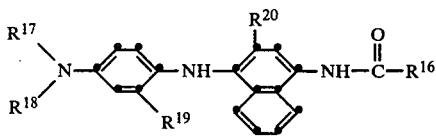

wherein $R^{16}$ is alkyl containing 1 to 25 carbon atoms, cycloalkyl containing 5 to 8 carbon atoms; aryl containing 6 to 25 carbon atoms; alkoxy containing 1 to 25 carbon atoms; aryloxy containing 6 to 25 carbon atoms; or

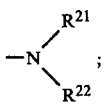

$R^{17}$ is hydrogen, alkyl containing 1 to 25 carbon atoms or acyl containing 2 to 25 carbon atoms;

$R^{18}$ is alkyl containing 1 to 25 carbon atoms or acyl containing 2 to 25 carbon atoms;

$R^{19}$ is hydrogen or alkyl containing 1 to 25 carbon atoms;

$R^{20}$ is hydrogen, carboxamido or alkyl containing 1 to 25 carbon atoms; and, $R^{21}$ and $R^{22}$ are individually hydrogen, alkyl containing 1 to 25 carbon atoms, aryl containing 6 to 25 carbon atoms or together are the atoms selected from the group consisting of carbon, hydrogen, nitrogen and oxygen atoms necessary to complete a 5 or 6 member heterocyclic group, such as morpholino, piperizino and pyrrolidino.

Examples of useful color-forming dye precursors according to the invention include:

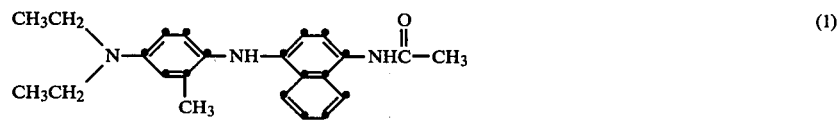
(1)

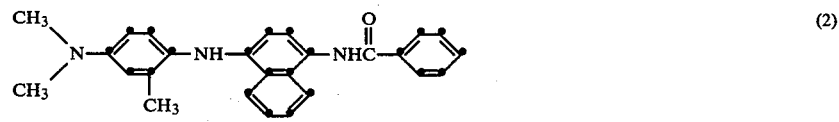
(2)

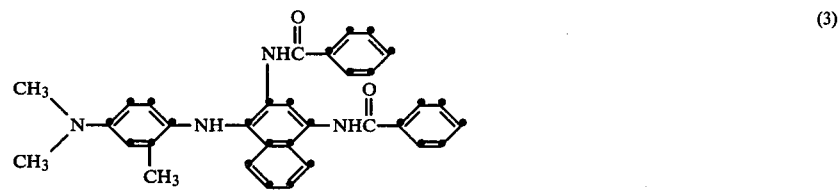
(3)

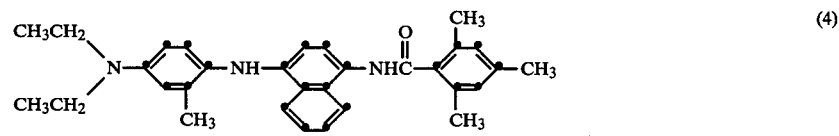
(4)

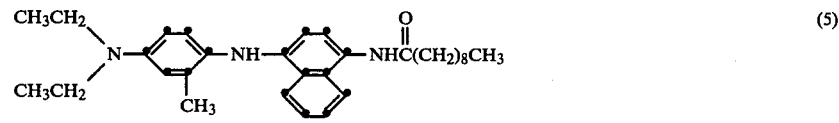
(5)

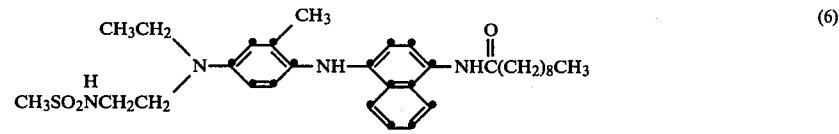
(6)

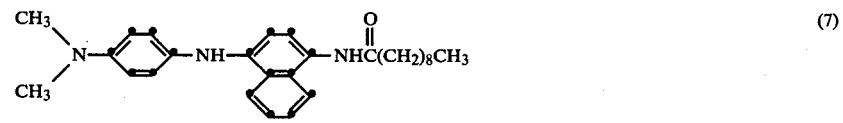
(7)

-continued
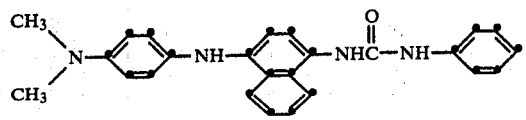 (8)
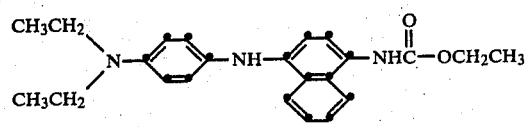 (9)
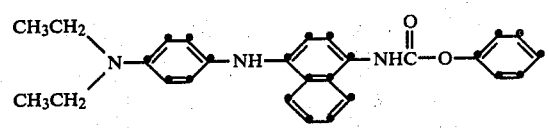 (10)
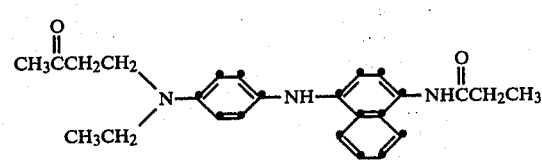 (11)
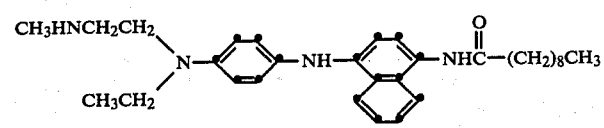 (12)
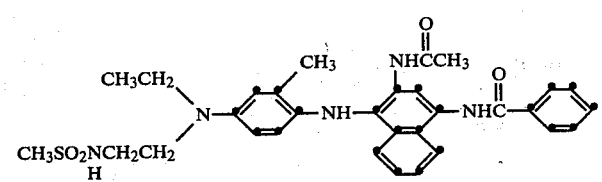 (13)
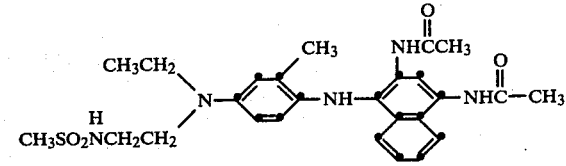 (14)
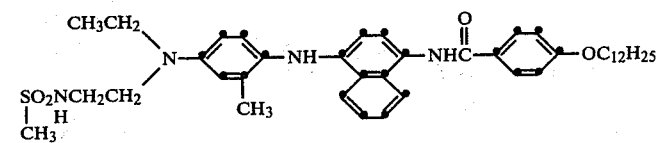 (15)
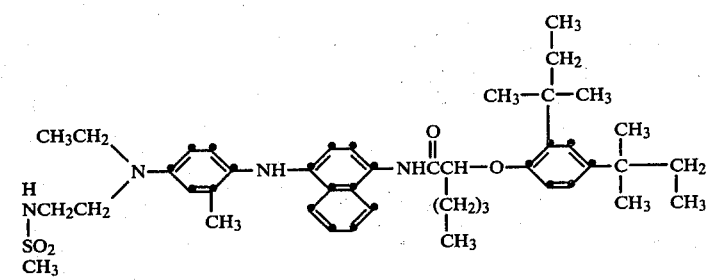 (16)
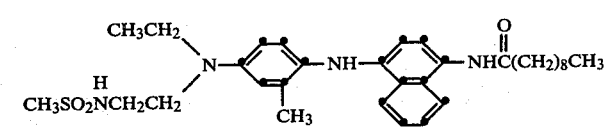 (17)

-continued
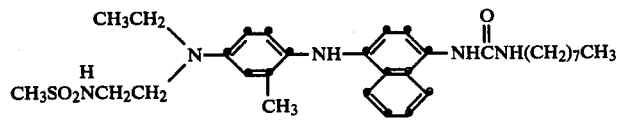 (18)
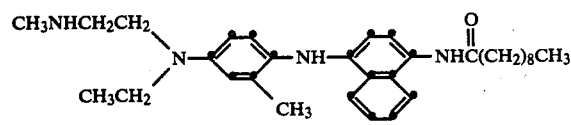 (19)
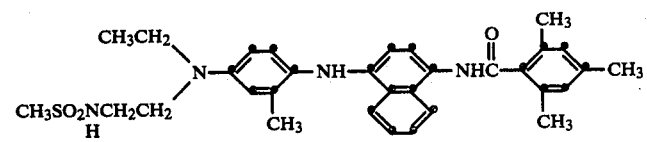 (20)
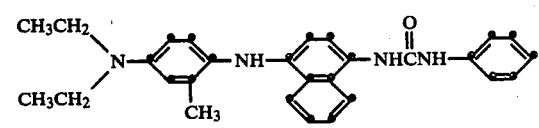 (21)
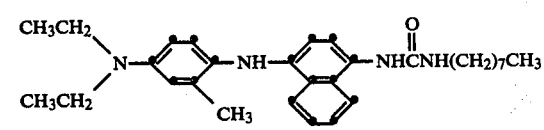 (22)
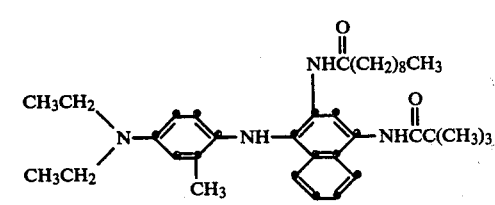 (23)
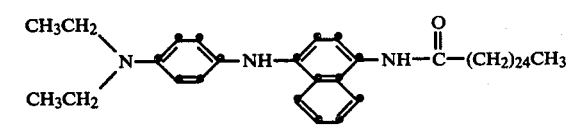 (24)
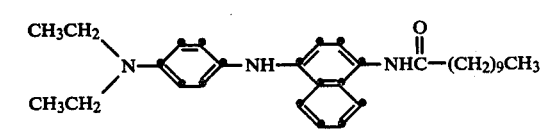 (25)
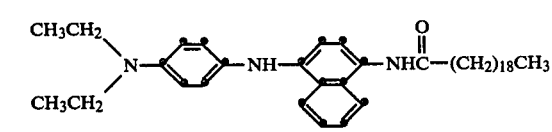 (26)
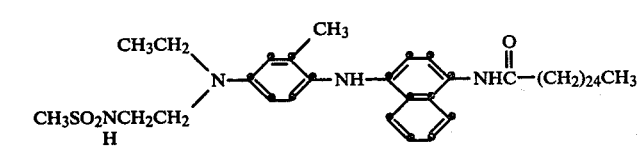 (27)
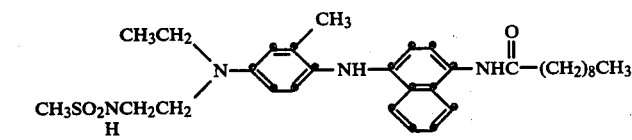 (28)

-continued
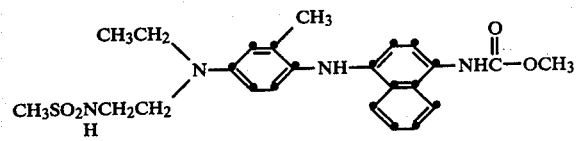 (29)
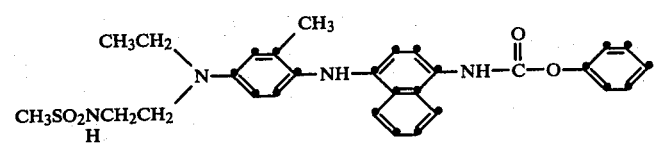 (30)
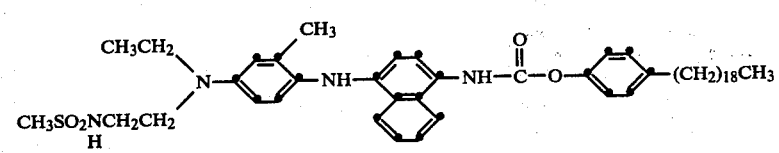 (31)
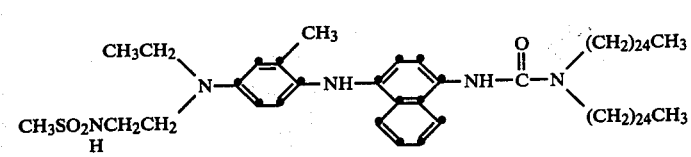 (32)
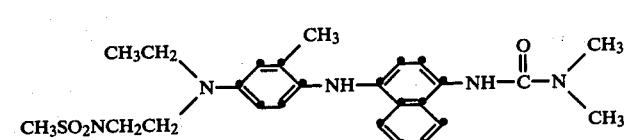 (33)
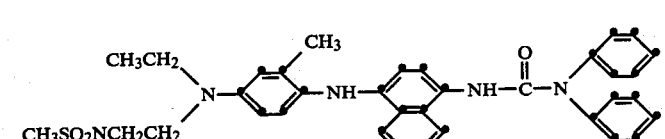 (34)
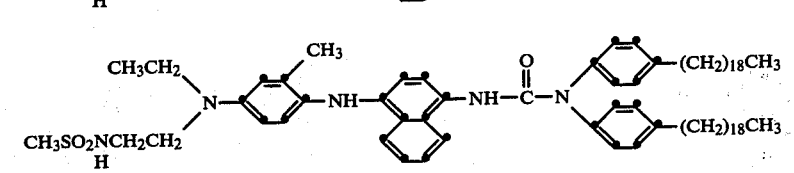 (35)
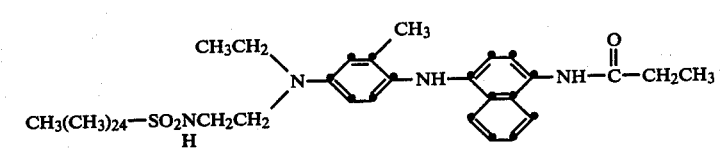 (36)
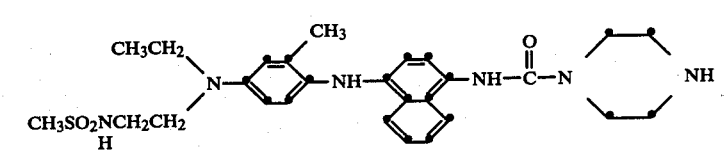 (37)
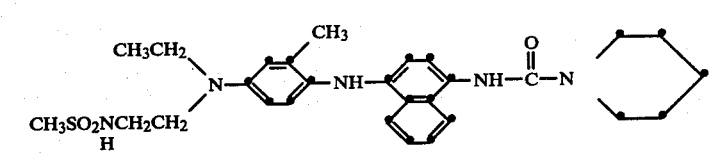 (38)
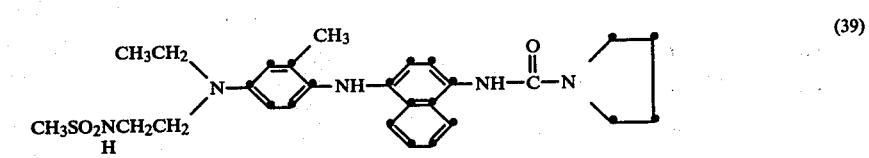 (39)

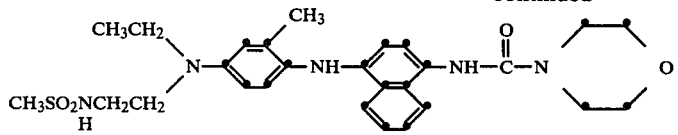 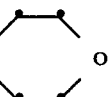 (40)

An especially useful embodiment of this invention is a photographic element comprising a support having thereon, in reactive association, in a gelatino binder: (a) photosensitive silver halide; and (b) a color-forming dye precursor which is imagewise converted upon exposure and processing of the element to a dye by cross-oxidation by means of a cross-oxidizing developing agent wherein the color-forming dye precursor is a 4-(4'-secondary or tertiary-amino)-anilino-1-carboxamidonaphthalene consisting essentially of a dye precursor represented by the formula:

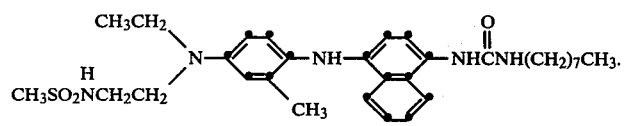

A carboxamido group herein means a group represented by the formula:

wherein $R^{23}$ is a substituent which does not adversely affect the color-forming dye precursor or imide dye according to the invention. R is, for example, alkyl containing 1 to 20 carbon atoms, such as methyl, ethyl, propyl, butyl, decyl, and eicosyl, or aryl containing 6 to 20 carbon atoms, such as phenyl and tolyl. Examples of such groups include phenylcarboxamido, methylcarboxamido and tolylcarboxamido.

A sulfonamido group herein means an unsubstituted sulfonamido group or a sulfonamido group that is substituted by a group that does not adversely affect the desired properties of the color-forming dye precursor according to the invention. A sulfonamido group herein means, for example, a group represented by the structure:

—NHSO$_2$Z wherein

Z is a substituent, such as alkyl containing 1 to 25 carbon atoms, for example methyl, ethyl, propyl, butyl, decyl and eicosyl, and aryl containing 6 to 25 carbon atoms, such as phenyl, tolyl and naphthyl. Examples of sulfonamido groups include methylsulfonamido, tolylsulfonamido, 2,4,6-triethylphenylsulfonamido, and 2,4,6-triisopropylsulfonamido.

A carbamoyl group herein means an unsubstituted carbamoyl group or a carbamoyl group that is substituted by a group that does not adversely affect the desired properties of the color-forming dye precursor according to the invention. A carbamoyl group herein means; for example, a group represented by the structure:

wherein $R^{24}$ is a substituent, such as alkyl containing 1 to 25 carbon atoms, for example methyl, ethyl, propyl, butyl, decyl and eicosyl, and aryl containing 6 to 25 carbon atoms, such as phenyl, tolyl and naphthyl. Examples of carbamoyl groups include methylcarbamoyl, ethylcarbamoyl, and phenylcarbamoyl.

A sulfamoyl group herein means an unsubstituted sulfamoyl group or a sulfamoyl group that is substituted by a group that does not adversely affect the desired properties of the color-forming dye precursor according to the invention. A sulfamoyl group herein means, for example, a group represented by the structure:

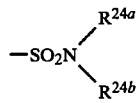

wherein $R^{24a}$ and $R^{24b}$ are individually hydrogen or a substituent, such as alkyl containing 1 to 25 carbon atoms, for example methyl, ethyl, propyl, butyl, decyl and eicosyl, or aryl containing 6 to 25 carbon atoms, such as phenyl, tolyl and xylyl. Examples of sulfamoyl groups include: —SO$_2$NH$_2$, —SO$_2$NHCH$_3$, —SO$_2$NHCH$_2$CH$_3$,

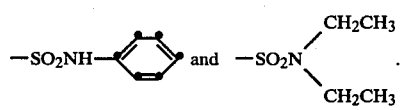

The color-forming dye precursors are prepared by condensation of a phenylenediamine compound with a substituted halonitronaphthalene wherein the nitro group is in the 4 position with respect to a halogen atom on the naphthalene ring, followed by reduction of the nitro group and subsequent formation of the amidonaphthalene from the intermediate amine.

An illustrative method of preparation of a color-forming dye precursor according to the invention is the preparation of 4{-4-[N-(2-methylsulfonamidoethyl)ethylamino]-2-methylanilino}-1-(N'-octylureido)-naphthalene as follows: 4-[N-(2-methylsulfonamidoethyl)ethylamino]-2-methylaniline (54.2 g, 0.2 mol) and 4-fluoro-1-nitronaphthalene (32.2 g, 0.2 mol) were stirred at 85° C. under nitrogen with pyridine (31.6 g, 0.4 mol) in dimethylsulfoxide (500 ml) for 24 hours. The resulting mixture is then poured into ice water and extracted with a suitable solvent, such as methylene chloride. The extract is washed with water, dried and concentrated. The resulting intermediate product is purified, such as by crystallization from ethanol to produce a purified intermediate (m.p. 170°–172° C.). The resulting intermediate is reduced in dry tetrahydrofuran containing a catalytic amount of palladium on charcoal at 40 psi (276 kPa) hydrogen pressure in a Parr apparatus. After removal of the catalyst, such as by filtration, octyl isocyanate is added to the filtrate. The mixture is stirred for 16 hours, water (100 ml) is added and the product is taken up in ether. The resulting solution is dried, filtered and concentrated. The resulting product is purified, such as by recrystallization from methanol. The purified compound has a melting point of 132°–133° C.

Another example of a preparation according to the invention is the preparation of 4-(4'-N,N-diethylamino-2-methylanilino-1-decanamidonaphthalene. This preparation is as follows:

4-(4-N,N-diethylamino-2-methylanilino)-1-nitronaphthalene (12 g., 0.0034 mole) is reduced in tetrahydrofuran (200 ml) on a Parr apparatus by means of a catalyst, such as palladium on charcoal, at 40 pounds per square inch (276 kPa) hydrogen pressure. The catalyst is then removed. Acid acceptor, such as triethylamine (11.2 ml, 0.08 mole) is added. Then decanoyl chloride (12.7 g., 0.0037 mole) in tetrahydrofuran (50 ml) is added dropwise. The resulting mixture is stirred until reaction completion, such as for about 16 hours. Water is added and the product taken up with a solvent, such as ether. Following drying and concentration of the solvent solution, the residue is typically purified, such as by recrystallization from ethanol and then methanol, to produce a white crystalline product having a melting point of 147° to 148° C.

The color-forming 4-(4'-secondary or tertiary-amino)anilino-1-carboxamidonaphthalene dye precursors are useful in a photographic material and process according to the invention in a range of concentrations. Selection of an optimum concentration of color-forming 4-(4'-secondary or tertiary-amino)anilino-1-carboxamidonaphthalene dye precursor or combination of such dye precursors depends upon the desired image, the particular photographic material, processing steps and conditions, other components in the photographic material, and the particular 4-(4'-secondary or tertiary-amino)-anilino-1-carboxamidonaphthalene dye precursor. A preferred concentration of dye precursor is within the range of about 0.1 to about 0.6 mole of color-forming dye precursor per mole of photosensitive silver halide in the photographic material. An especially useful concentration of color-forming dye precursor is within the range of about 0.1 to about 0.2 mole of color-forming dye precursor per mole of silver halide in the photographic material. In a photographic element, a preferred concentration of color-forming dye precursor is within the range of about 0.5 to about 22 mg of color-forming dye precursor per square decimeter of support, such as a concentration within the range of about 5 to about 11 mg per square decimeter of support.

The hue of the dye produced from the color-forming dye precursor will vary, depending upon such factors as the particular groups on the color-forming dye precursor, processing conditions, other components in the photographic material such as dispersion solvents, and whether a combination of dyes is present in the photographic material or not. The color-forming dye precursor in the photographic material is preferably colorless prior to exposure and processing. Some of the suitable color-forming dye precursors have a slight color, such as a slight yellow color, in the photographic material. This slight color is not considered unacceptable.

The term "colorless" herein means that the color-forming dye precursor in the photographic material does not absorb radiation to an undesired degree in the visible region of the electromagnetic spectrum. In some photographic materials, the color-forming dye precursor absorbs radiation in certain areas of the electromagnetic spectrum which do not adversely affect the desired properties or the desired image formed upon processing.

The color-forming dye precursor generally absorbs electromagnetic radiation outside the visible region of the electromagnetic spectrum before imagewise exposure and processing of the photographic material. The nature of the absorption and degree of absorption of the color-forming dye precursor depends upon the nature, for the most part, of the substituent groups on the color-forming dye precursor.

The photographic materials according to the invention comprise a photosensitive component which consists essentially of photographic silver halide. Examples of useful photographic silver halides are silver chloride, silver bromide, silver bromoiodide, silver chlorobromoiodide, silver iodide and mixtures thereof. The photographic silver halide is generally present in the photographic material in the form of an emulsion which is a dispersion of the photographic silver halide in a suitable binder. The photographic silver halide is present in a range of grain sizes from fine grain to coarse grain. Negative and direct positive photographic silver halide emulsions are useful in photographic materials according to the invention. Such photographic emulsions are described in, for example, *Research Disclosure*, December, 1978, Item No. 17643. A composition containing the photographic silver halide is prepared by any of the well known procedures in the photographic art, such as described in *Research Disclosure*, December 1978, Item No. 17643.

The photographic material according to the invention contains addenda commonly found to be useful in silver halide photographic materials. These addenda include chemical sensitizers, brighteners, antifoggants, emulsion stabilizers, light absorbing and scattering materials, hardeners, coating aids, plasticizers, lubricants, antistatic materials, matting agents, and development modifiers, as described in *Research Disclosure*, December 1978, Item No. 17643.

The photographic silver halide is generally spectrally sensitized by means of spectral sensitizing dyes, as described in, for example, *Research Disclosure*, December 1978, Item No. 17643. Useful spectral sensitizing dyes in photographic materials according to the invention include such dyes as polymethine dyes which include the cyanines, merocyanines, complex cyanines and merocyanines (including tri, tetra and polynuclear cyanines and merocyanines), as well as oxonols, hemioxonols, styryls, merostyryls and streptocyanines. Combinations of spectral sensitizing dyes are also useful in photographic materials according to the invention.

The photographic silver halide is useful in a range of concentrations in a photographic material according to the invention. An optimum concentration of photographic silver halide depends upon such factors as the desired image, processing conditions, particular dye precursor, other components of the photographic material and particular photographic silver halide. A useful concentration of photographic silver halide in the photographic material according to the invention is generally within the range of about 2 to about 7 moles of photographic silver halide per mole of color-forming dye precursor in the photographic material. The coverage of photographic silver halide is less than otherwise might be required, due to the enhancing properties of the dye produced upon processing of the photographic material according to the invention.

The color-forming dye precursor is in any suitable location in a photographic material according to the invention which produces the desired dye upon processing. The color-forming dye precursor is, if desired, in a layer contiguous to the layer comprising the photosensitive silver halide. The term "in reactive association" herein means that the photosensitive silver halide and the color-forming dye precursor are in a location with respect to each other which enables the photographic material according to the invention upon processing to produce a desired dye image and a desired silver image.

The color-forming dye precursor is frequently immobilized in an oil phase in the photographic material. This enables the dye precursor to be dispersed satisfactorily. Alternatively, the color-forming dye precursor is dispersed in a dispersion solvent to produce a desired photographic material. Coupler solvents known in the photographic art are useful for aiding dispersion of the color-forming dye precursor. Examples of useful coupler solvents include N-n-butylacetanilide, diethyl lauramide, di-n-butyl phthalate and 2,4-di-tertiaryamylphenol. The color-forming dye precursor is also usefully loaded into a latex or a non-solvent dispersion is prepared, if desired.

Many developing agents are useful for developing an image in a photographic material according to the invention. Any silver halide developing agent is useful according to the invention, provided it comprises a cross-oxidizing developing agent which will cross-oxidize with the color-forming dye precursor. Such a silver halide developer, called herein a cross-oxidizing developing agent, becomes oxidized during development by reducing exposed silver halide to silver metal. The oxidized developer then cross-oxidizes the color-forming dye precursor to form the desired dye.

A cross-oxidizing developing agent (COD) enables the color-forming dye precursor to become oxidized without the color-forming dye precursor itself developing silver. The cross-oxidizing developing agent is viewed alternatively as an electron transfer agent which shuttles electrons between the developing silver halide and the color-forming dye precursor.

The requirements for a cross-oxidizing developing agent generally are: (a) the developing agent must have sufficient electrochemical potential under the conditions of use to develop exposed silver halide, (b) in its oxidized form, the developing agent must be of such electrochemical potential as to oxidize the color-forming dye precursor, and (c) in its oxidized form, the developing agent must be stable to decomposition by other chemical reactions for a sufficient period to undergo the redox reaction with the color-forming dye precursor. Whether a developing agent is a cross-oxidizing developing agent or not depends upon whether the oxidized form is sufficiently stable and the oxidizing potential is such that an effective transferral of electrons occurs through whatever phase barriers exist during cross-oxidizing development. Whether a particular developing agent meets these requirements depends upon the conditions under which development occurs. Other factors influence whether a particular developing agent is a cross-oxidizing developer, including the pH of the developing composition, the temperature of the development process and the length of development time. Examples of developing agents which are useful as cross-oxidizing developing agents include 3-pyrazolidione developers, such as 1-phenyl-3-pyrazolidone, 1-phenyl-4,4-dimethyl-3-pyrazolidone and 4-hydroxymethyl-4-methyl-1-phenyl-3-pyrazolidone. Such cross-oxidizing developing agents are described in, for example, U.S. Pat. No. 3,938,995. Combinations of non-cross-oxidizing developing agents and cross-oxidizing developing agents are useful, provided a minor proportion of the non-cross-oxidizing developing agent is present, such as less than about 10 percent of the total combination is non-cross-oxidizing developing agent. Examples of combinations of a non-cross-oxidizing developing agent and a cross-oxidizing developing agent include 4-hydroxymethyl-4-methyl-1-phenyl-3-pyrazolidone with a minor proportion of at least one of the following non-cross-oxidizing developing agents: ascorbic acid, hydroquinone and pyrimidine. Selection of an optimum cross-oxidizing silver halide developing agent or developing agent combination will depend upon such factors as the desired image, the particular photosensitive silver halide, processing conditions, and the particular color-forming dye precursor.

A silver halide developing agent or silver halide developing agent combination is incorporated in the photographic material according to the invention, if desired. Generally, the silver halide developing agent is most useful in a processing solution in which the photographic material according to the invention is processed after exposure.

The developing agent is useful in a range of concentration in the photographic material or in a processing composition in which the photographic material according to the invention is processed. A preferred concentration of developing agent in the photographic material is within the range of about 0.01 to about 1.0 mole of developing agent per mole of color-forming dye precursor in the photographic material. A preferred concentration of developing agent in a processing solution for processing a photographic material containing a color-forming dye precursor is within the range of about 0.5 to about 2 grams of developing agent per liter of processing solution.

The term "developing agent" herein includes compounds which are developing agents or developing agent precursors. That is, those compounds are included which are not developing agents in the photographic material until a condition occurs, such as contact with a suitable activator for the photographic material.

The tone of the silver image and dye image produced in a photographic material according to the invention will vary, depending upon such factors as the silver morphology of the developed silver image, the covering power of the silver materials, the particular dye formed, the particular developing agent, processing conditions, and other components in the photographic material. In photographic materials according to the invention that provide a brown silver image, a dye produced is especially useful which is complementary in hue to the silver image. A combination of dyes and a silver image that produce a neutral-appearing image are generally most useful.

The photographic materials according to the invention comprise a variety of binders alone or in combination. The binders include both naturally occurring substances, such as proteins, for example, gelatin, gelatin derivatives, cellulose derivatives, polysaccharides, such as dextran, and gum arabic; but also include synthetic polymeric materials, such as water-soluble polyvinyl compounds, like poly(vinylpyrrolidone) and acrylamide polymers. Examples of useful binders include those described in, for instance, *Research Disclosure*, December 1978, Item No. 17643.

The photographic elements according to the invention generally contain an overcoat layer, and/or interlayer, and/or subbing layer to provide desired properties. The overcoat layer, for example, increases resistance to abrasion and other markings on the element. The overcoat layer, interlayer or subbing layer contain, alone or in combination, the described binders.

A photographic element according to the invention comprises a variety of supports. Useful supports include those that are resistant to adverse changes in structure due to processing conditions and which do not adversely affect the desired sensitometric properties of the photographic materials. Examples of useful supports include cellulose ester, poly(vinylacetal), poly(ethylene terephthalate) and polycarbonate films, as well as related films and resinous materials. Glass, paper and metal supports are also useful. A flexible support is generally most useful.

Photographic materials according to the invention are generally coated on a support by procedures known in the photographic art. Such procedures include, for example, immersion or dip coating, roller coating, reversal roll coating, airknife coating, doctor blade coating, spray coating, extrusion coating, bead coating, stretch flow coating and curtain coating.

Photographic elements according to the invention are imagewise exposed by means of various forms of energy to produce a developable image. Such forms of energy include those to which the photosensitive silver halide is sensitive, and encompass ultraviolet, visible and infrared regions of the electromagnetic spectrum, as well as electron beam and beta radiation, gamma ray, X-ray, alpha particle, neutron radiation and other forms of corpuscular wave-like radiant energy in either coherent or non-coherent forms. Lasers are useful, for example. Exposures are monochromatic, orthochromatic or panchromatic, depending on the spectral sensitization of the photosensitive silver halide. Imagewise exposure is generally for a sufficient time and intensity to produce a developable latent image in the photographic material.

A photographic element according to the invention is processed in (a) a process which produces a positive dye image, (b) in a process which produces a negative dye image and negative silver image, (c) in a process which produces a negative dye image, or (d) in a process which produces a positive dye image and a positive silver image. The light-sensitive silver halide in the photographic material according to the invention is processed following exposure to form a visible image. This is done, for example, by associating the silver halide at one stage of the process with an aqueous alkaline medium in the presence of a cross-oxidizing developing agent contained in the medium and/or in the photographic material.

To produce a positive dye image, also known as a reversal dye image, according to the invention, it is generally desirable to process the exposed photographic material by means of a non-cross-oxidizing developing composition as a first development step. During this step, the exposed silver halide is reduced to elemental silver by the non-cross-oxidizing developing composition. The non-cross-oxidizing developing composition does not, when oxidized, oxidize the color-forming dye precursor according to the invention to its corresponding dye.

The non-cross-oxidizing developer composition useful in this step is generally an alkaline solution, preferably an aqueous solution comprising a non-cross-oxidizing developing agent. Non-cross-oxidizing developing agents are known in the photographic art and include many silver halide developing agents which will reduce exposed photosensitive silver halide to silver, but will not oxidize the color-forming dye precursor to a corresponding dye. Examples of useful non-cross-oxidizing developing agents are described in, for example, *Research Disclosure*, December 1978, Item No. 17643. Useful non-cross-oxidizing developers include developer compositions comprising ascorbic acid, hydroquinone, pyrimidine developing agents and a combination of hydroquinone and N-methyl-p-aminophenol.

In a second step of a process for forming a positive dye image according to the invention, fogging of the photographic material is accomplished by exposing the photographic material to light or by chemical fogging by means of chemical fogging agents known in the photographic art.

Following the described fogging step, a second silver halide developing step is carried out. This is carried out by means of a cross-oxidizing developing composition. It is in this step that the color-forming dye precursor is converted to a dye in the image areas. Any silver halide developing composition is useful in this step, provided that it cross-oxidizes the color-forming dye precursor to a desired dye. Such silver halide developing compositions include alkaline solutions comprising a cross-oxidizing silver halide developing agent, preferably a 3-pyrazolidone cross-oxidizing silver halide developing agent. This cross-oxidizing developing agent becomes oxidized during development by reducing exposed or fogged silver halide to silver metal. The oxidized developing agent then cross-oxidizes the color-forming dye precursor to a desired dye. The photographic material, upon processing, contains a concentration of dye in inverse proportion to the amount of exposure of the photographic element. That is, a positive dye image, also described herein as a reversal dye image, is formed.

An especially useful process for producing a positive dye image in an imagewise exposed photographic element according to the invention comprises: (a) developing the exposed photographic element in an alkaline photographic developer in the absence of a cross-oxidizing silver halide developing agent, and then (b) uniformly exposing the resulting element to a flash exposure of light, followed by (c) developing the photographic element in an alkaline, cross-oxidizing developer, comprising an aqueous, alkaline solution of 4-methyl-4-hydroxymethyl-1-phenyl-3-pyrazolidone, and (d) bleaching and fixing the photographic element in a silver halide bleaching and fixing solution to produce a positive dye image in a photographic element. It is generally useful to treat the photographic element by means of a development stop bath after step (a) and before step (b).

Photographic elements according to the invention are also useful for producing negative dye images. Such negative dye images are produced in an exposed photographic element comprising a support having thereon, in reactive association, in binder, (a) photosensitive silver halide, and (b) a color-forming 4-(4'-secondary or tertiary-amino)anilino-1-carboxamidonaphthalene dye precursor by (A) developing the photographic element in an alkaline, cross-oxidizing photographic silver halide developer composition to produce a negative dye image and silver image; then (B) removing at least part of the silver image from the photographic element, such as by bleaching and fixing the silver from the element. Removal of the silver is accomplished by means of bleaching and fixing compositions known in the photographic art. The optimum bleaching and fixing compositions are selected to provide the desired dye image. Suitable bleaching and fixing compositions are described in Grant Haist, *Modern Photographic Processing,* Vol. 2, Chapter 10 (1979). The bleaching agent employed should be of such strength that it does not oxidize the color-forming dye precursor and thereby lead to uniform dye density in the element.

Photographic elements according to the invention comprising direct-positive photographic silver halide are useful for forming positive, dye images and positive, silver images. A process of producing a positive, dye image and a positive, silver image in an imagewise exposed photographic element comprising a support having thereon, in reactive association, in binder, (a) direct-positive photographic silver halide, and (b) a color-forming 4-(4'-secondary or tertiary-amino)anilino-1-carboxamidonaphthalene dye precursor, comprising (A) developing the photographic element in an alkaline, cross-oxidizing photographic silver halide developing composition; then (B) fixing the resulting photographic element to produce a positive, dye image and a positive, silver image. Useful direct-positive silver halide is described in, for example, *Research Disclosure,* December 1978, Item No. 17643, pages 22 through 31. Fixing the photographic element is accomplished by means of fixing compositions known in the photographic art, such as a sodium thiosulfate fixing composition.

An advantage of the photographic material and process according to the invention is that the dye images produced upon processing possess desired stability to post-processing conditions and visible light exposure. A simple test is useful for establishing the degree of stability which is desired for a dye image produced from a color-forming dye precursor according to the invention. One such test is a test well known in the photographic art in which a processed photographic element is exposed to a Simulated Average North American Skylight (SANS) with continuous 5400 LUX of exposure at an average temperature of 21° C. at 45 percent relative humidity. A comparison of the stability of the tested dye is then observed.

When a cross-oxidizing silver halide developing agent is present in the photographic material according to the invention, a developed image is produced after imagewise exposure of the photographic material by contacting the material with an alkaline activator solution which enables development of the exposed silver halide, as well as production of the desired dye. Many alkaline activators are useful for developing an image in a photographic material according to the invention comprising an incorporated cross-oxidizing silver halide developing agent. Alkaline activators which are known to be useful in the photographic art, such as in stabilization processing, are useful for developing an image in the described photographic material according to the invention. Examples of useful alkaline activators include sodium hydroxide, potassium hydroxide, trisodium phosphate.12H$_2$O (pH 12), sodium metaborate (pH 12), disodium phosphate and monosodium phosphate. An optimum alkaline activator will depend upon such factors as the desired image, the particular cross-oxidizing developing agent, processing conditions and the particular color-forming dye precursor. An especially useful alkaline activator comprises trisodium phosphate (pH 12).

The alkaline activator is useful in a range of concentrations. A generally useful concentration of alkaline activator is within the range of about 10 to about 50 grams per liter of activator solution which produces a pH within the range of about 11 to about 12. An optimum concentration of alkaline activator will depend upon such factors as the desired image, the particular activator, processing conditions, particular cross-oxidizing developing agent, particular photosensitive silver halide and particular color-forming dye precursor.

After exposure and processing of the photographic material according to the invention, the photographic material comprises a new dye image or, alternatively, a new dye image and a silver image. The dye image consists essentially of a dye represented by the formula:

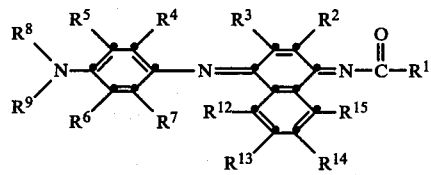

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined.

Examples of useful naphthoquinoneimide dyes in exposed and processed photographic materials according to the invention are as follows:

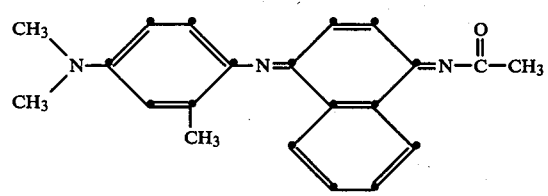

(1)

(2)
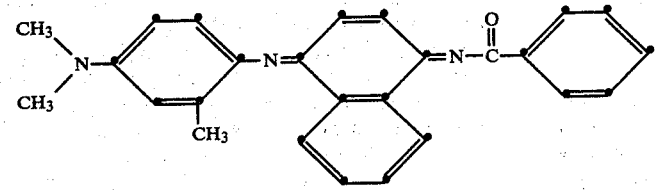
(3)
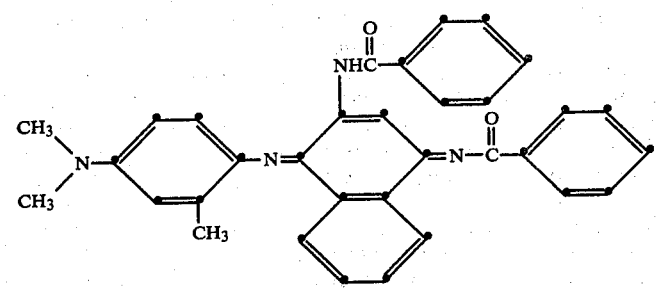
(4)
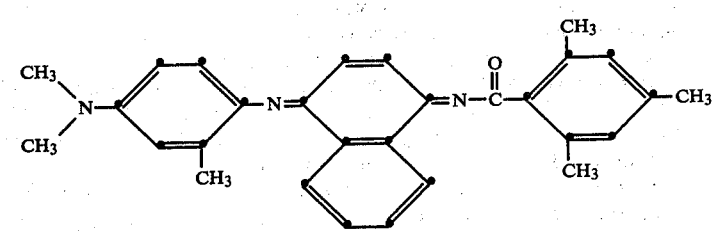
(5)
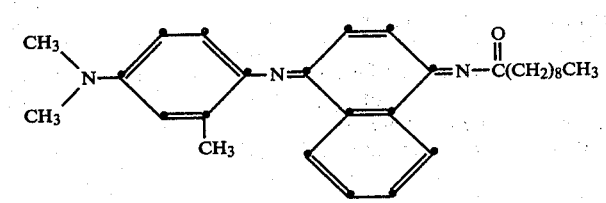
(6)
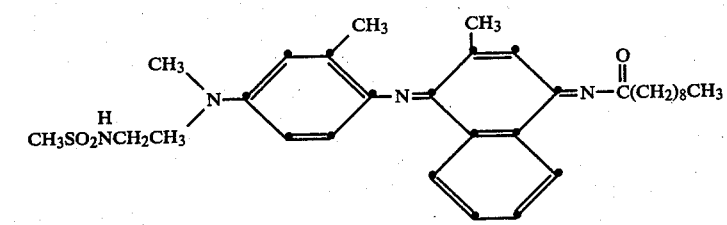
(7)
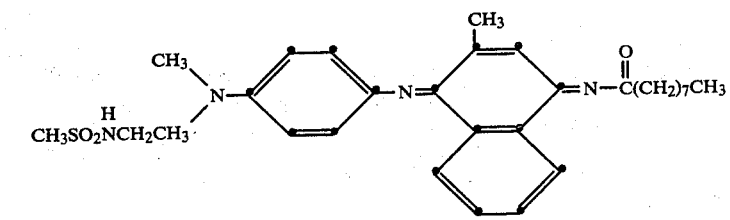
(8)
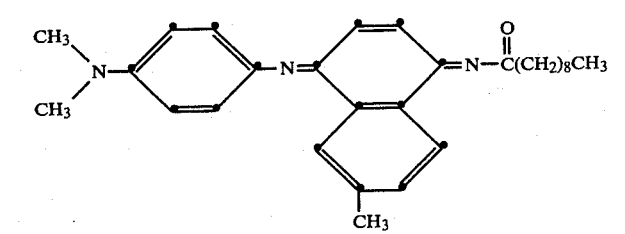

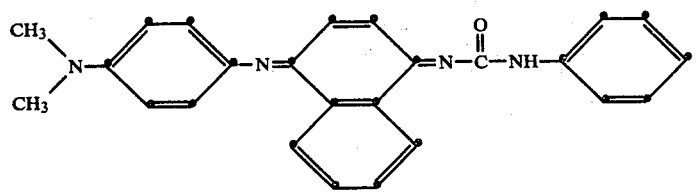
(9)
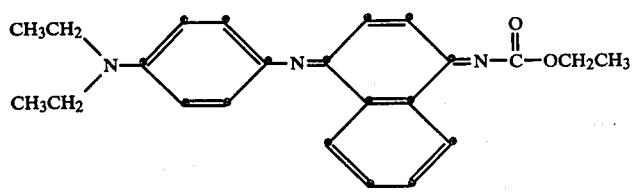
(10)
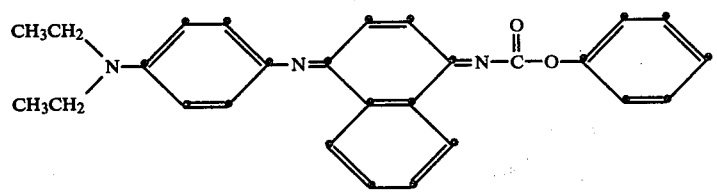
(11)
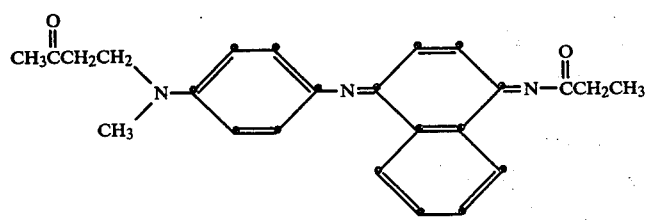
(12)
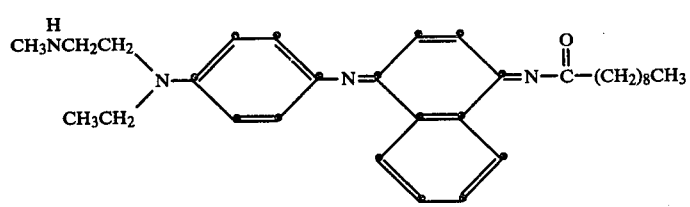
(13)
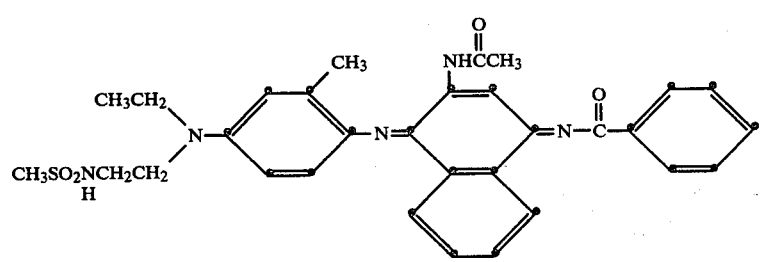
(14)
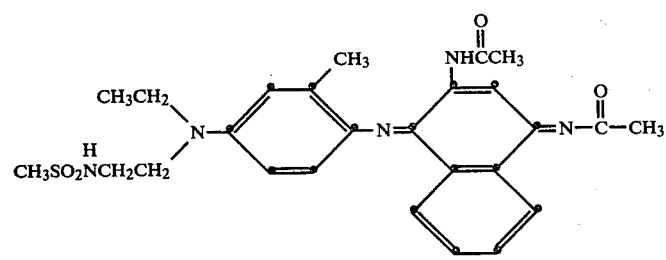
(15)

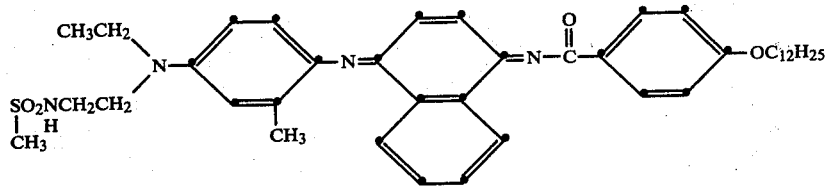
(16)
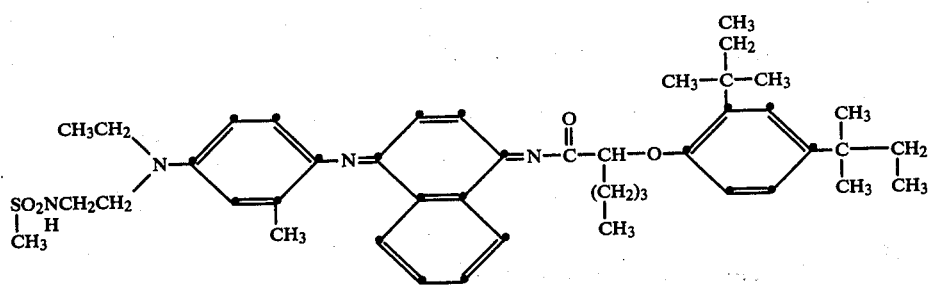
(17)
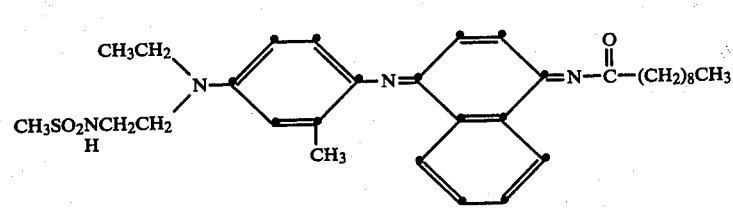
(18)
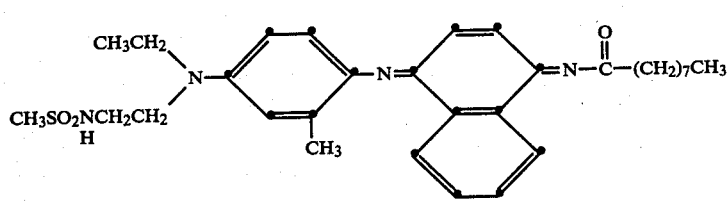
(19)
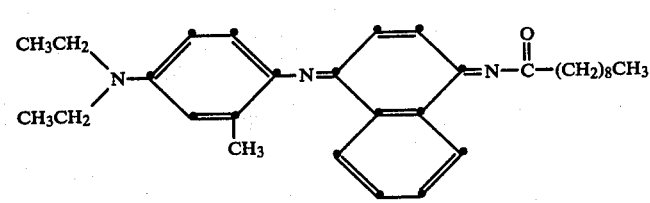
(20)
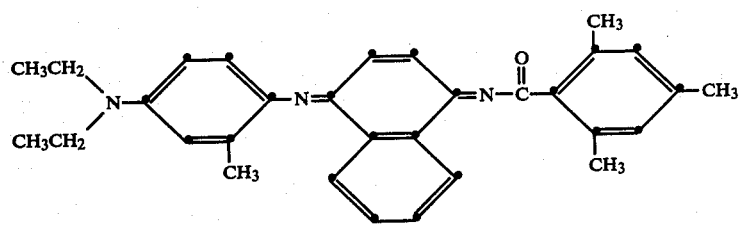
(21)
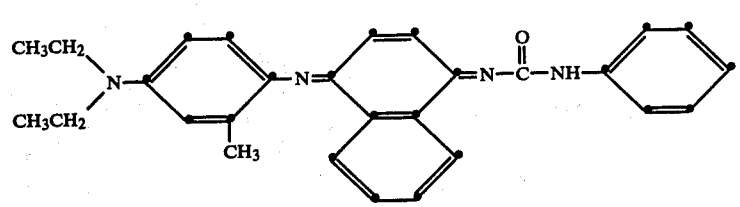
(22)

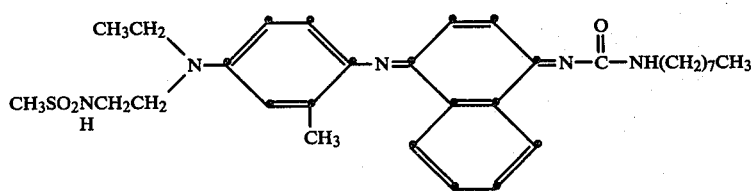
(23)
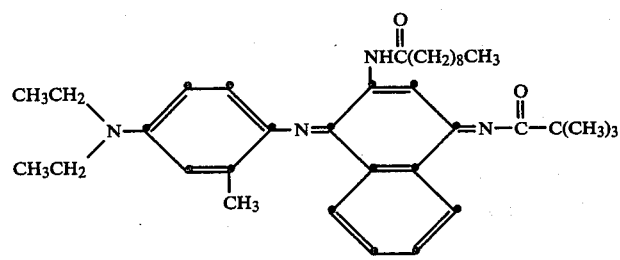
(24)
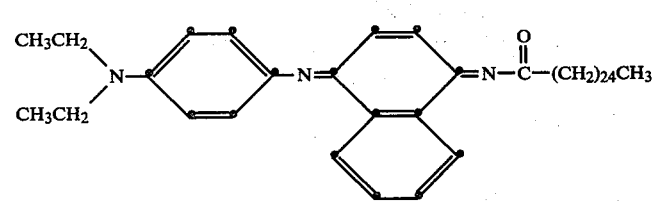
(25)
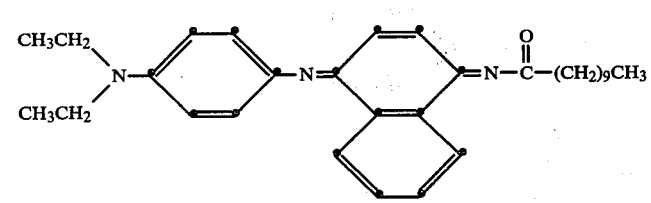
(26)
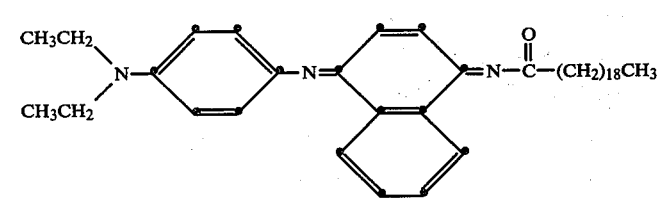
(27)
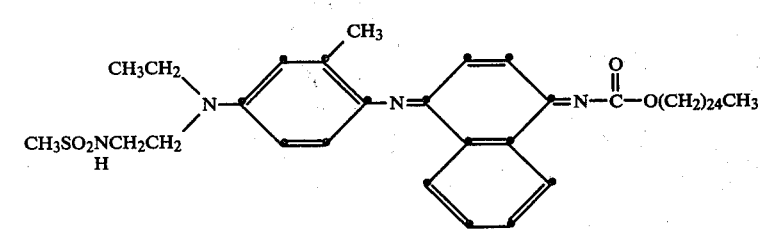
(28)
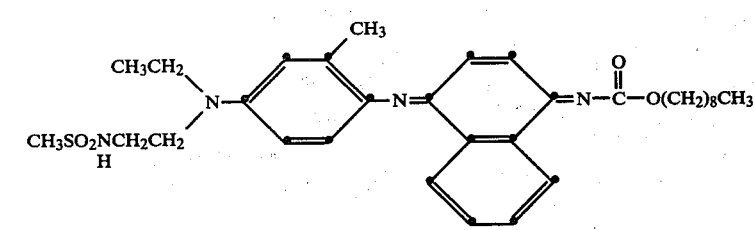
(29)

-continued
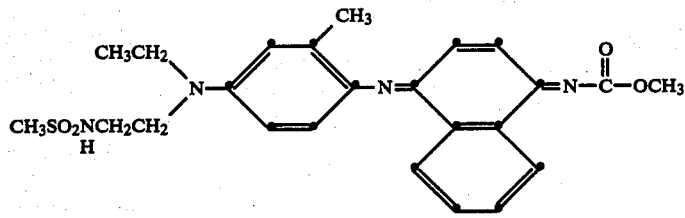
(30)
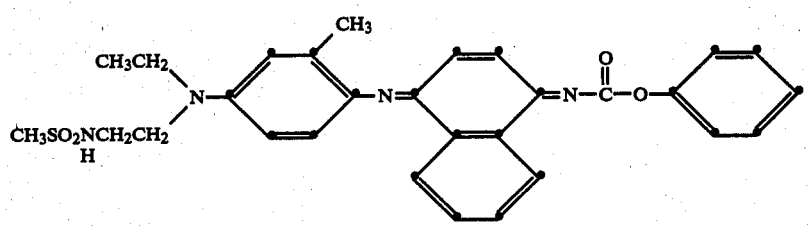
(31)
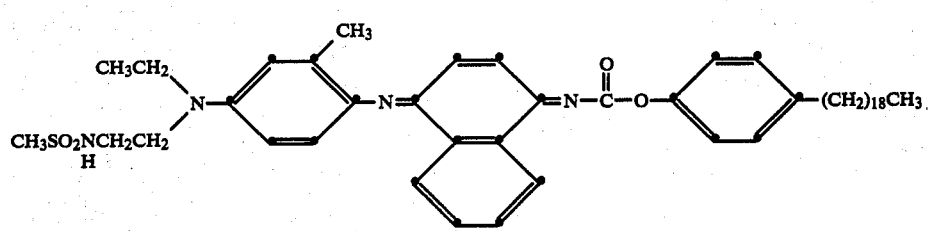
(32)
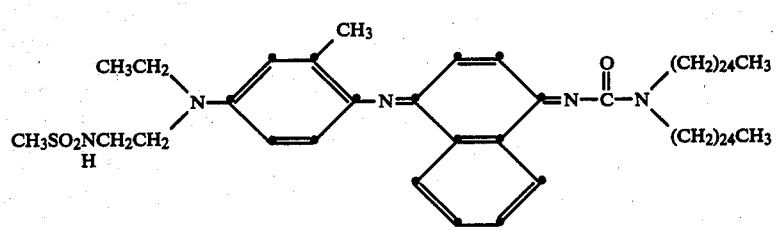
(33)
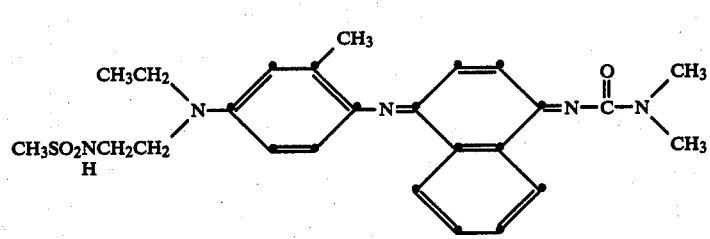
(34)
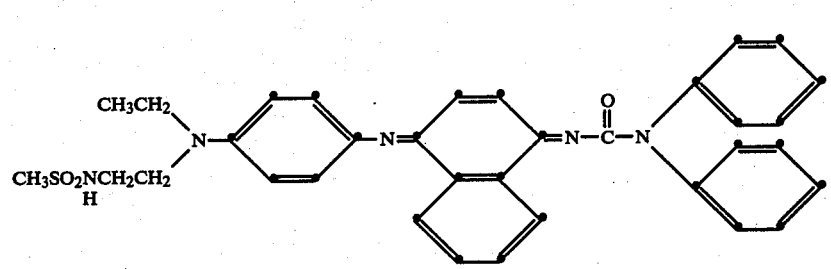
(35)
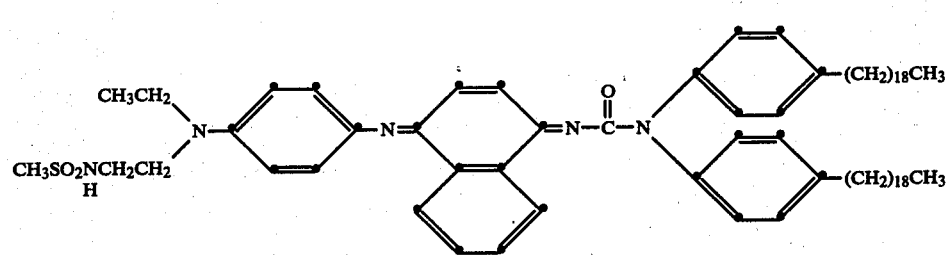
(36)

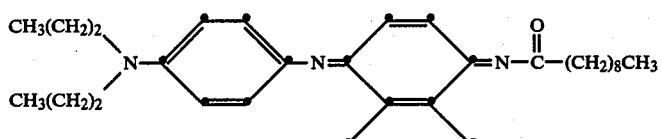
(37)

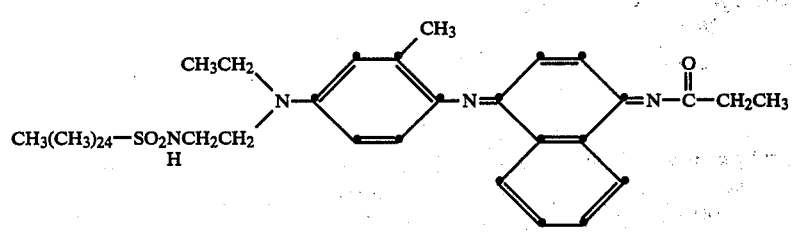
(38)

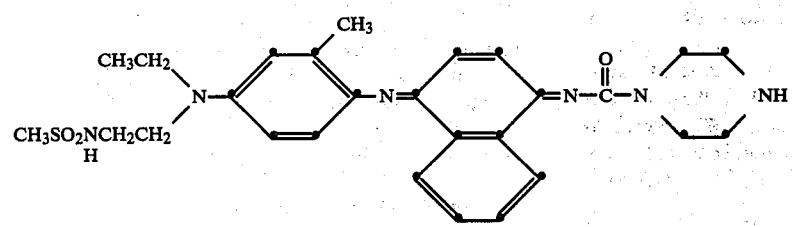
(39)

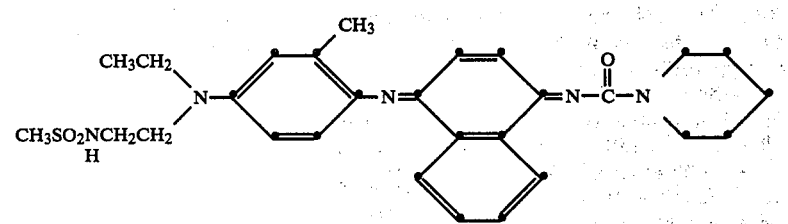
(40)

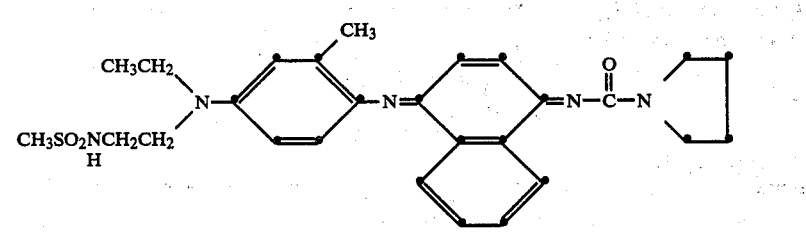
(41)

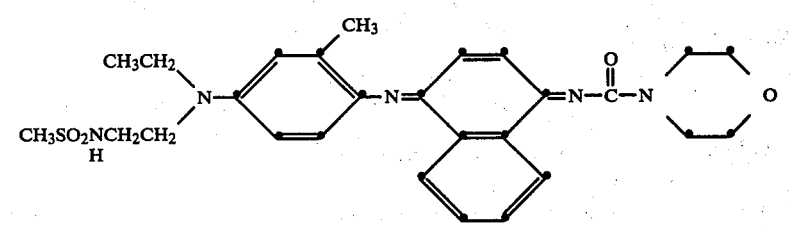
(42)

The naphthoquinoneimide dyes according to the invention have increased stability to hydrolysis compared to corresponding benzoquinoneimide dyes. This is believed to be due at least in part to the resistance which naphthoquinoneimide dyes exhibit to formation of a resonance structure that favors formation of an indoaniline dye.

The following examples are included for a further understanding of the invention.

EXAMPLE 1

Preparation of
4-{4'-[N-(2-methylsulfonamidoethyl)ethylamino]-2-methylanilino}-1-(N'-octylureido)-naphthalene

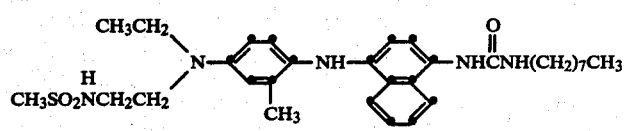

A solution of 4-[N-(2-methylsulfonamidoethyl)ethylamino]-2-methylaniline (54.2 g, 0.2 mol) and 4-fluoro-1-nitronaphthalene (32.2 g, 0.2 mol) with pyridine (31.6 g, 0.4 mol) in dimethylsulfoxide (500 ml) was stirred and heated under a nitrogen atmosphere at 85° C. for 24 hours. The reaction mixture was then poured into ice water and extracted with methylene chloride. The extract was washed three times with water, dried, and concentrated. After crystallization from ethanol, an intermediate product (30.4 g, 34% yield, m.p. 171°–173° C.) was characterized by nuclear magnetic resonance, mass spectral and elemental analysis.

A sample of the resulting intermediate (6.0 g, 0.014 mol) was reduced in dry tetrahydrofuran (150 ml) containing a catalytic amount of palladium on charcoal at 40 psi hydrogen pressure in a Parr Apparatus. After removal of the catalyst by filtration, octyl isocyanate (2.1 g, 0.014 mol) was added to the filtrate. The mixture was stirred for 16 hours, then water (100 ml) was added and the product was taken up in ether. The ethereal solution was dried, filtered and concentrated. The residue was recrystallized twice from methanol. The crystalline product (4.7 g, 59% yield, m.p. 132°–133° C.) was characterized by nuclear magnetic resonance and elemental analysis.

EXAMPLE 2

Preparation of
4-(4'-N,N-diethylamino-2-methylanilino)-1-decanamidonaphthalene

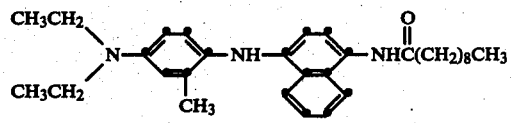

4-(4-N,N-diethylamino-2-methylphenyl-amino)-1-nitronaphthalene (5.0 g, 0.014 mol) was reduced in tetrahydrofuran (200 ml) in a Parr Apparatus using palladium on charcoal catalyst at 40 psi hydrogen pressure. After removal of the catalyst by filtration, first triethylamine (3 g, 0.03 mol) was added and then decanoyl chloride (3.0 g, 0.016 mol) in tetrahydrofuran (50 ml) was added dropwise. The mixture was stirred for 16 hours. Then water (150 ml) was added and the product taken up with ether. Following drying (by means of $Na_2SO_4$), filtration and concentration of the ether solution, the residue was recrystallized from ethanol and then methanol. The resulting white crystalline product (2.4 g, 36% yield, m.p. 147°–148° C.) was characterized by nuclear magnetic resonance, mass spectral and elemental analysis.

EXAMPLES 3–7

Use in Photographic Element

In each of the following examples a photographic element was prepared by coating the following photographic composition on a subbed poly(ethyleneterephthalate) film support:

(1) silver bromoiodide (0.8 micron grain, sulfur and gold chemically sensitized) (9.7 mg/dm²)

(2) color-forming dye precursor as coupler solvent dispersion (1:1 to 1:2 parts by volume) (3.0 to 16.2 mg/dm²) (coverage of dispersion was adjusted to give an approximate silver plus dye density of 2.0)

(3) photographic gelatin (binder) (43.2 mg/dm²), hardened by bis(vinylsulfonylmethyl)ether (($CH_2$=$CHSO_2CH_2$)$_2$O) (2.0 parts by weight in 200 parts water, 0.43 mg/dm²). Each photographic element was chemically oxidized at 22° C. in the following processing sequence:

(1) 30 second fix in the following fixing composition:

| | grams per liter |
|---|---|
| $NaS_2O_3 \cdot 5H_2O$ | 248.0 |
| $Na_2CO_3 \cdot H_2O$ | 30.0 |
| $NaHCO_3$ | 5.0 |
| pH 10.0 | |

(2) 60 second water wash (3) 30 second oxidizing treatment in the following oxidizing composition:

a sodium phosphate buffer (pH 12.0) containing

| | |
|---|---|
| $K_3Fe(CN)_6$ | 10 g/liter |
| benzyl alcohol | 10 ml/liter |
| potassium bromide | 1 g/liter |
| water to one liter | |

(4) 5 minute water wash (5) 10 second water wash (in Kodak Photo-Flo ® Solution, which is a trademark of and available from Eastman Kodak Company, U.S.A.)

(6) dry in air at room temperature (about 21° C.).

The resulting dried photographic elements were then exposed (emulsion side to the light) to 5400 LUX irradiation (Simulated Average North American Skylight irradiation) for 1, 3 and 7 days. Density was measured at the maximum absorption wavelength for each dye. The percentage of dye fade was calculated based on the following formula:

$$\% \text{ Fade} = \left[ \frac{D_{initial} - D_{faded}}{D_{initial}} \right] 100\%$$

wherein D equals density. Results of these examples are summarized in following Table I:

TABLE I

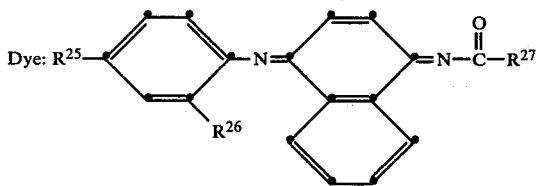

| Example No. (λ max of dye, nm) | R²⁵ | R²⁶ | R²⁷ | % Fade (Days) 1 | 3 | 7 |
|---|---|---|---|---|---|---|
| 3 (595) | $(CH_3CH_2)_2N-$ | $-CH_3$ | $-C(CH_2)_8CH_3$ | 3.48 | 14.5 | 36.3 |
| 4 (586) | $CH_3CH_2$\\N—\\/$CH_3SO_2NCH_2CH_2$\\H | $-CH_3$ | $-(CH_2)_8CH_3$ | 12.7 | 28.2 | 54.0 |
| 5 (604) | $CH_3CH_2$\\N—\\/$CH_3SO_2NCH_2CH_2$\\H | $-CH_3$ | (branched alkoxyphenyl group) | 3.23 | 11.2 | 17.1 |
| 6 (616) | $(CH_3CH_2)_2N-$ | $-CH_3$ | (trimethylphenyl group) | 3.23 | 11.2 | 27.1 |
| 7 (576) | $CH_3CH_2$\\N—\\/$CH_3SO_2NCH_2CH_2$\\H | $-CH_3$ | $-NH(CH_2)_7CH_3$ | 0.35 | 1.18 | 1.53 |

EXAMPLES 8–10

The dyes listed in following Table II were prepared by procedures similar to those described:

TABLE II

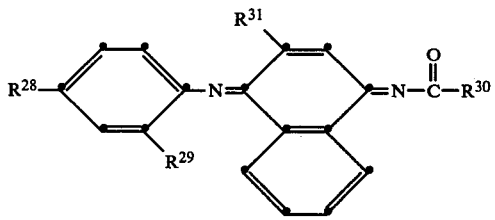

| Example No. (λ max of dye, nm) | R²⁸ | R²⁹ | R³⁰ | R³¹ |
|---|---|---|---|---|
| 8 (593) | $CH_3CH_2$\\N—\\/$CH_3SO_2NCH_2CH_2$\\H | $-CH_3$ | —⟨phenyl⟩—$OC_{12}H_{25}$ | H |
| 9 (601) | $(CH_3CH_2)_2N-$ | $-CH_3$ | $-NH-$⟨phenyl⟩ | H |

TABLE II-continued

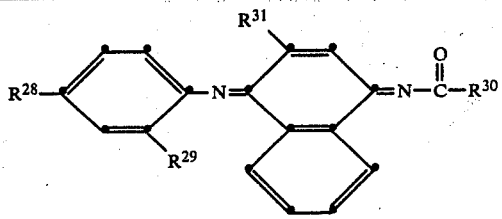

| Example No. (λ max of dye, nm) | R[28] | R[29] | R[30] | R[31] |
|---|---|---|---|---|
| 10 (582) | $(CH_3CH_2)_2N-$ | $-CH_3$ | $-C(CH_3)_3$ | $-NHC(O)(CH_2)_8CH_3$ |

EXAMPLES 11–16

In each of the following Examples a photographic element was prepared as described in Examples 3–7. The photographic element in each case was imagewise exposed to light to produce a developable latent image in the photographic element. The exposed element was then processed at 22° C. in the following processing sequence:

(1) 30-second development by immersion in the following composition:

| | |
|---|---|
| tribasic sodium phosphate 12-hydrate | 47.5 g |
| 4-hydroxymethyl-4-methyl-1-phenyl-3-pyrazolidone (cross-oxidizing developing agent) | 1 g |
| benzyl alcohol | 10 ml |
| potassium bromide | 1 g |
| water to one liter | |

(2) 2-minute water wash
(3) 30-second fix in the fixing composition described in step 1 of Example 3
(4) 2-minute water wash
(5) dry in air at room temperature (about 21° C.).

The resulting dried photographic elements were then exposed (emulsion side to the light) to 5400 LUX irradiation (Simulated Average North American Skylight irradiation) for 1, 3 and 7 days. Density was measured at the maximum absorption wavelength for each dye. The percentage of dye fade was calculated as described in Example 3. A dye image and silver image was produced in each example. Results of the percentage of dye fade are summarized in following Table III:

TABLE III

| Example No. and Dye | % Fade, Days | | |
|---|---|---|---|
| | 1 | 3 | 7 |
| 11 (dye of Example 3) | 7.35 | 17.6 | 35.5 |
| 12 (dye of Example 4) | 12.8 | 25.7 | 44.2 |
| 13 (dye of Example 5) | 19.7 | 31.8 | 33.8 |
| 14 (dye of Example 6) | 2.59 | 9.34 | 21.9 |
| 15 (dye of Example 7) | 0.28 | 0.62 | 1.86 |
| 16 (dye of Example 8) | 1.19 | 2.76 | 8.14 |

The following compounds were prepared by procedures similar to those described in Examples 1 and 2:

TABLE IV

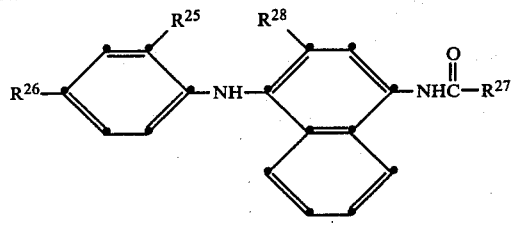

| Example No. | R[25] | R[26] | R[27] | R[28] | melting point °C. |
|---|---|---|---|---|---|
| 17 | $CH_3$ | $CH_3CH_2\!\!-\!\!N\!\!-\!\!CH_3CH_2$ | 2,4,6-tri($CH_3$)phenyl | H | 198–199 |
| 18 | $CH_3$ | $CH_3CH_2\!\!-\!\!N\!\!-\!\!CH_3SO_2NCH_2CH_2\!\!-\!\!H$ | $(CH_2)_8CH_3$ | H | 100–101 |

TABLE IV-continued

[Structure with R25, R26, R27, R28 substituents on naphthalene-aniline with NHC(O)R27 group]

| Example No. | R25 | R26 | R27 | R28 | melting point °C. |
|---|---|---|---|---|---|
| 19 | CH₃ | CH₃CH₂\N—<br>CH₃SO₂NCH₂CH₂ / H | —⟨phenyl⟩—OC₁₂H₂₅ | H | 133–135 |
| 20 | CH₃ | CH₃CH₂\N—<br>CH₃SO₂NCH₂CH₂ / H | —CH—O—⟨aryl with t-Bu, t-pentyl groups⟩<br>(CH₂)₃<br>CH₃ | H | 135–137 |
| 21 | CH₃ | CH₃CH₂\N—/CH₃CH₂ | —NH—⟨phenyl⟩ | H | 232–234 |
| 22 | CH₃ | CH₃CH₂\N—/CH₃CH₂ | —C(CH₃)₃ | —NHC(O)(CH₂)₈CH₃ | 191–192 |

The invention has been described in detail with particular reference to preferred embodiments thereof, but it will be understood that variations and modifications can be effected within the spirit and scope of the invention.

What is claimed is:

1. In a photographic element comprising a support having thereon, in reactive association, photographic silver halide and a carboxamido color-forming dye precursor which is imagewise converted upon exposure and processing of said element to a dye; the improvement comprising:
  as said dye precursor, a 4-(4'-secondary or tertiary-amino)anilino-1-carboxamidonaphthalene color-forming dye precursor which forms a naphthoquinoneimide dye.

2. In a photographic element comprising a support having thereon, in reactive association, photographic silver halide and a carboxamido color-forming dye precursor which is imagewise converted upon exposure and processing of said element to a dye; the improvement comprising:
  as said dye precursor, a carboxamido color-forming dye precursor represented by the formula:

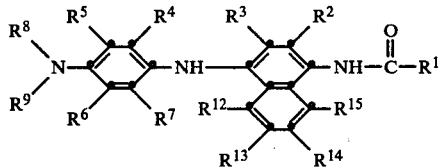

wherein:

$R^1$ is alkyl containing 1 to 25 carbon atoms, cycloalkyl containing 5 to 8 carbon atoms, aryl containing 6 to 25 carbon atoms, alkoxy containing 1 to 25 carbon atoms, aryloxy containing 6 to 25 carbon atoms,

or a 5 or 6 member heterocyclic group;

$R^2$, $R^3$, $R^4$, $R^5$, $R^6$, and $R^7$ are individually hydrogen, alkyl containing 1 to 25 carbon atoms, aryl containing 6 to 25 carbon atoms, alkoxy containing 1 to 25 carbon atoms, arylsulfonyl containing 6 to 25 carbon atoms, chlorine, bromine, carbamoyl, sulfamoyl, carboxy, and carboxamido;

$R^8$ is hydrogen, alkyl containing 1 to 25 carbon atoms, aryl containing 6 to 25 carbon atoms, acyl containing 2 to 25 carbon atoms, or carbamoyl containing 2 to 25 carbon atoms;

$R^9$ is alkyl containing 1 to 25 carbon atoms, aryl containing 6 to 25 carbon atoms, acyl containing 2 to 25 carbon atoms, or carbamoyl;

$R^{10}$ and $R^{11}$ are individually hydrogen, alkyl containing 1 to 25 carbon atoms, aryl containing 6 to 25 carbon atoms, a carbocyclic group containing 6 to 8 carbon atoms, or taken together represent the atoms necessary to complete a 5 or 6 member heterocyclic ring;

$R^{12}$, $R^{13}$, $R^{14}$, and $R^{15}$ are individually hydrogen, alkyl containing 1 to 25 carbon atoms, cyano, sulfamoyl, chlorine, carboxamido, sulfonamido, bromine and alkoxy containing 1 to 25 carbon atoms.

3. A photographic element as in claim 1 also comprising a binder.

4. A photographic element as in claim 1 also comprising a silver halide developing agent.

5. A photographic element as in claim 1 wherein said color-forming dye precursor consists essentially of a compound represented by the formula:

$R^{16}$ is alkyl containing 1 to 25 carbon atoms; aryl containing 6 to 25 carbon atoms, alkoxy containing 1 to 25 carbon atoms, aryloxy containing 6 to 25 carbon atoms, or $$-N\begin{matrix}R^{21}\\R^{22}\end{matrix};$$

$R^{17}$ is hydrogen, alkyl containing 1 to 25 carbon atoms, or acyl containing 2 to 25 carbon atoms;

$R^{18}$ is alkyl containing 1 to 25 carbon atoms or acyl containing 2 to 25 carbon atoms;

$R^{19}$ is hydrogen or alkyl containing 1 to 25 carbon atoms;

$R^{20}$ is hydrogen, carboxamido or alkyl containing 1 to 25 carbon atoms; and, $R^{21}$ and $R^{22}$ are individually hydrogen, alkyl containing 1 to 25 carbon atoms, aryl containing 6 to 25 carbon atoms or together are the atoms necessary to complete a 5 or 6 member heterocylic group.

6. A photographic element as in claim 1 wherein said color-forming dye precursor consists essentially of a compound represented by the formula:

7. A photographic element as in claim 1 wherein said color-forming dye precursor consists essentially of a compound represented by the formula:

8. A photographic element as in claim 1 wherein said color-forming dye precursor consists essentially of a compound represented by the formula:

9. A photographic element as in claim 1 wherein said color-forming dye precursor consists essentially of a compound represented by the formula:

10. A photographic element as in claim 1 also comprising in reactive association, in binder, with said photosensitive silver halide, a cross-oxidizing, photographic silver halide developing agent.

11. A photographic element as in claim 1 also comprising in reactive association, in binder, with said photosensitive silver halide, a 3-pyrazolidone, photographic silver halide developing agent.

12. In a photographic element comprising a support having thereon, in a gelatino binder, in reactive association, photographic silver halide and a carboxamido color-forming dye precursor, the improvement comprising:

as said dye precursor, a color-forming dye precursor represented by the formula:

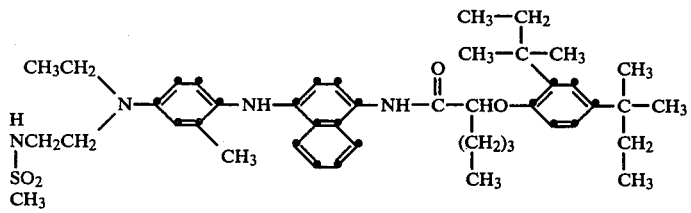

13. In a photographic element comprising a support having thereon, in a gelatino binder, in reactive association, a photographic silver halide gelatino emulsion and a carboxamido color-forming dye precursor, the improvement comprising:
as said dye precursor, a color-forming dye precursor represented by the formula:

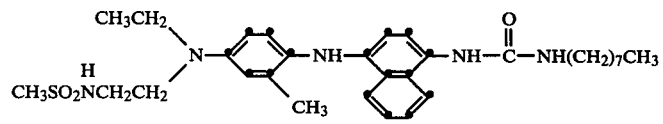

14. In a photographic element comprising a support having thereon, in a gelatino binder, in reactive association, photographic silver halide and a carboxamido color-forming dye precursor, the improvement comprising:
as said dye precursor, a color-forming dye precursor represented by the formula:

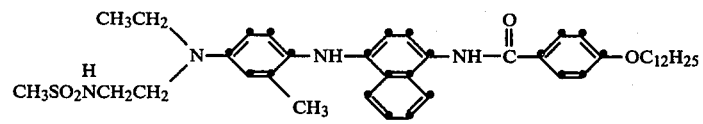

15. In a photographic composition comprising a photographic silver halide and a carboxamido color-forming dye precursor; the improvement comprising:
as said dye precursor, a 4-(4′-secondary or tertiary-amino)anilino-1-carboxamidonaphthalene color-forming dye precursor which forms a naphthoquinoneimide dye.

16. In a photographic composition comprising photographic silver halide and a carboxamido color-forming dye precursor; the improvement comprising:
as said dye precursor, a carboxamido color-forming dye precursor represented by the formula:

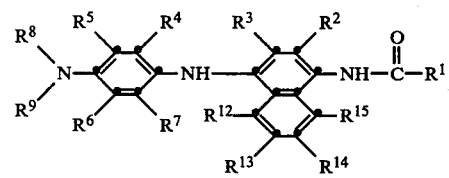

wherein:

$R^1$ is alkyl containing 1 to 25 carbon atoms, cycloalkyl containing 5 to 8 carbon atoms, aryl containing 6 to 25 carbon atoms, alkoxy containing 1 to 25 carbon atoms, aryloxy containing 6 to 25 carbon atoms,

or a 5 or 6 member heterocyclic group;

$R^2$, $R^3$, $R^4$, $R^5$, $R^6$, and $R^7$ are individually hydrogen, alkyl containing 1 to 25 carbon atoms, alkoxy containing 1 to 25 carbon atoms, nitro, arylsulfonyl containing 6 to 25 carbon atoms, chlorine, bromine, carbamoyl, sulfamoyl, carboxy, and carboxamido;

$R^8$ is hydrogen, alkyl containing 1 to 25 carbon atoms, aryl containing 6 to 25 carbon atoms, acyl containing 2 to 25 carbon atoms, or carbamoyl containing 2 to 25 carbon atoms;

$R^9$ is alkyl containing 1 to 25 carbon atoms, aryl containing 6 to 25 carbon atoms, acyl containing 2 to 25 carbon atoms, or carbamoyl;

$R^{10}$ and $R^{11}$ are individually hydrogen, alkyl containing 1 to 25 carbon atoms, aryl containing 6 to 25 carbon atoms, a carbocyclic group containing 6 to 8 carbon atoms, or taken together represent the atoms necessary to complete a 5 or 6 member heterocyclic ring;

$R^{12}$, $R^{13}$, $R^{14}$, and $R^{15}$ are individually hydrogen, alkyl containing 1 to 25 carbon atoms, cyano, sulfamoyl, chlorine, bromine, carboxamido, sulfonamido, and alkoxy containing 1 to 25 carbon atoms.

17. A photographic composition as in claim 15 also comprising a binder.

18. A photographic composition as in claim 15 also comprising a silver halide developing agent.

19. A photographic composition as in claim 15 wherein said color-forming dye precursor consists essentially of a compound represented by the formula:

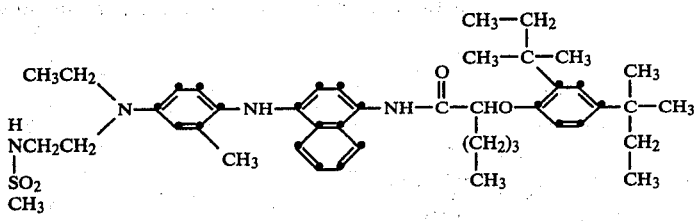

20. A photographic composition as in claim 15 wherein said color-forming dye precursor consists essentially of a compound represented by the formula:

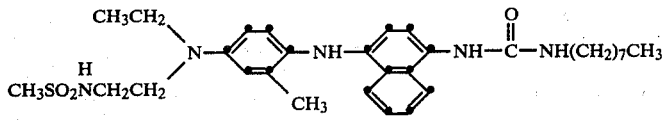

21. A photographic composition as in claim 15 wherein said color-forming dye precursor consists essentially of a compound represented by the formula:

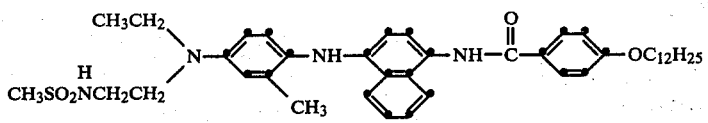

22. A photographic composition as in claim 15 wherein said color-forming dye precursor consists essentially of a compound represented by the formula:

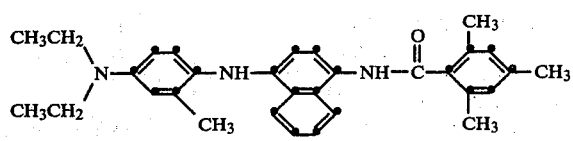

23. A photographic composition as in claim 15 also comprising a cross-oxidizing, photographic silver halide developing agent.

24. A photographic composition as in claim 15 also comprising a 3-pyrazolidone, photographic silver halide developing agent.

25. In a photographic composition comprising, in a binder, photographic silver halide and a carboxamido color-forming dye precursor; the improvement comprising:
as said dye precursor, a color-forming dye precursor represented by the formula:

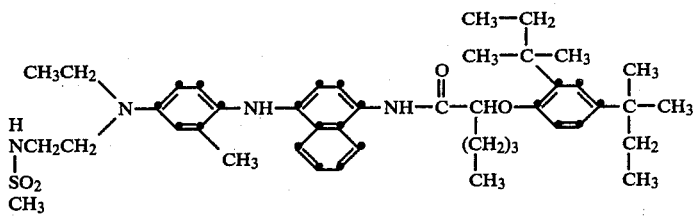

26. In a photographic composition comprising, in a binder, photographic silver halide and a carboxamido color-forming dye precursor; the improvement comprising:
as said dye precursor, a color-forming dye precursor represented by the formula:

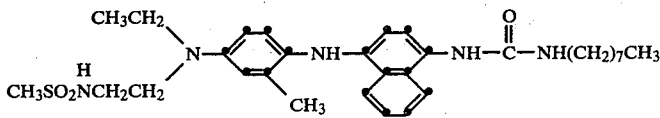

27. In a photographic composition comprising, in a binder, photographic silver halide and a carboxamido color-forming dye precursor; the improvement comprising:
as said dye precursor, a color-forming dye precursor represented by the formula:

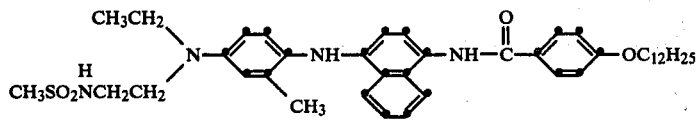

28. A process of producing a negative dye image and a negative silver image in an exposed photographic element comprising a support having thereon, in reactive association, in binder, photographic silver halide color-forming 4-(4'-secondary or tertiary-amino)anilino-1-carboxamidonaphthalene dye precursor which is converted upon processing of said element to a naphthoquinoneimide dye by cross-oxidation by means of a cross-oxidizing silver halide developing agent; said process comprising the step:

(A) developing said photographic element in an alkaline, cross-oxidizing, photographic silver halide developer composition to produce a negative naphthoqinoneimide dye image and silver image.

29. A process of producing a negative dye image and a negative silver image in an exposed photographic element comprising a support having thereon, in reactive association, in binder, photographic silver halide and a color-forming 4-(4'-secondary or tertiary-amino)anilino-1-carboxamidonaphthalene dye precursor represented by the formula:

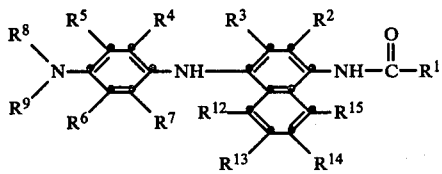

wherein:

$R^1$ is alkyl containing 1 to 25 carbon atoms, cycloalkyl containing 5 to 8 carbon atoms, aryl containing 6 to 25 carbon atoms, alkoxy containing 1 to 25 carbon atoms, aryloxy containing 6 to 25 carbon atoms,

or a 5 or 6 member heterocyclic group;

$R^2$, $R^3$, $R^4$, $R^5$, $R^6$, and $R^7$ are individually hydrogen, alkyl containing 1 to 25 carbon atoms, aryl containing 6 to 25 carbon atoms, alkoxy containing 1 to 25 carbon atoms, arylsulfonyl containing 6 to 25 carbon atoms, chlorine, bromine, carbamoyl, sulfamoyl, carboxy, and carboxamido;

$R^8$ is hydrogen, alkyl containing 1 to 25 carbon atoms, aryl containing 6 to 25 carbon atoms, acyl containing 2 to 25 carbon atoms, or carbamoyl containing 2 to 25 carbon atoms;

$R^9$ is alkyl containing 1 to 25 carbon atoms, aryl containing 6 to 25 carbon atoms, acyl containing 2 to 25 carbon atoms, or carbamoyl;

$R^{10}$ and $R^{11}$ are individually hydrogen, alkyl containing 1 to 25 carbon atoms, aryl containing 6 to 25 carbon atoms, a carbocyclic group containing 6 to 8 carbon atoms, or taken together represent the atoms necessary to complete a 5 or 6 member heterocyclic ring;

$R^{14}$, $R^{15}$, $R^{16}$, and $R^{17}$ are individually hydrogen, alkyl containing 1 to 25 carbon atoms, cyano, sulfamoyl, chlorine, carboxamido, sulfonamido, bromine and alkoxy containing 1 to 25 carbon atoms;

wherein said dye precursor is converted upon processing of said element to a dye by cross-oxidation by means of a cross-oxidizing silver halide developing agent, said process comprising the step:

(A) developing said photographic element in an alkaline, cross-oxidizing, photographic silver halide developer composition comprising a 3-pyrazolidone cross-oxidizing silver halide developing agent to produce a negative dye image and silver image.

30. A process as in claim 29 of producing a negative dye image and a negative silver image in an exposed photographic element comprising a support having thereon, in reactive association, in binder, photographic silver halide and a color-forming dye precursor represented by the formula:

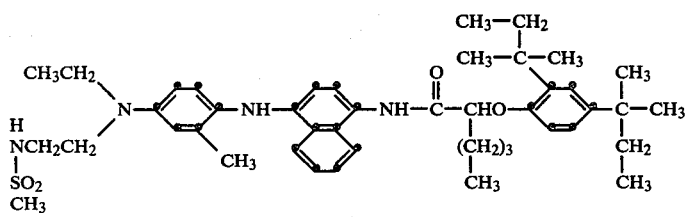

said process comprising the step:

(A) developing said photographic element in an aqueous, alkaline, cross-oxidizing photographic silver halide developer solution comprising a cross-oxidizing photographic silver halide developing agent consisting essentially of 4-methyl-4-hydroxymethyl-1-phenyl-3-pyrazolidone.

31. A process as in claim 29 of producing a negative dye image and a negative silver image in an exposed photographic element comprising a support having thereon, in reactive association, in binder, photographic silver halide and a color-forming dye precursor represented by the formula:

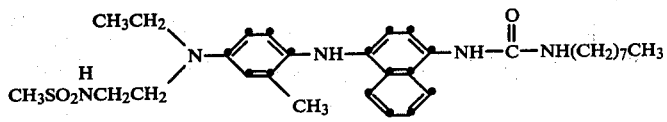

said process comprising the step:

(A) developing said photographic element in an aqueous, alkaline, cross-oxidizing photographic silver halide developer solution comprising a cross-oxidizing photographic silver halide developing agent consisting essentially of 4-methyl-4-hydroxymethyl-1-phenyl-3-pyrazolidone.

32. A process as in claim 29 of producing a negative dye image and a negative silver image in an exposed photographic element comprising a support having thereon, in reactive association, in binder, photographic silver halide and a color-forming dye precursor represented by the formula:

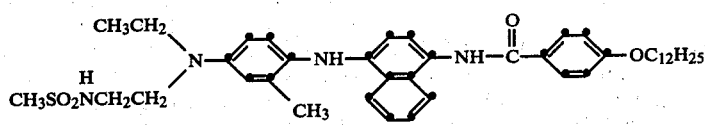

said process comprising the step:

(A) developing said photographic element in an aqueous, alkaline, cross-oxidizing photographic silver halide developer solution comprising a cross-oxidizing photographic silver halide developing agent consisting essentially of 4-methyl-4-hydroxymethyl-1-phenyl-3-pyrazolidone.

33. A process as in claim 29 of producing a negative dye image and a negative silver image in an exposed photographic element comprising a support having thereon, in reactive association, in binder, photographic silver halide and a color-forming dye precursor represented by the formula:

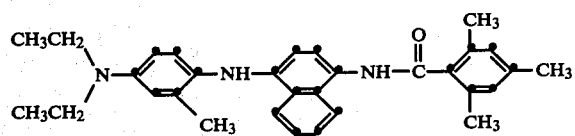

said process comprising the step of:

(A) developing said photographic element in an aqueous, alkaline, cross-oxidizing photographic silver halide developer solution comprising a cross-oxidizing photographic silver halide developing agent consisting essentially of 4-methyl-4-hydroxymethyl-1-phenyl-3-pyrazolidone.

34. A process of producing a positive, dye image in an imagewise exposed photographic element comprising a support having thereon, in reactive association, in binder, photographic silver halide and a color-forming 4-(4'-secondary or tertiary-amino)anilino-1-carboxamidonaphthalene which is converted upon processing of said element to a naphthoquinoneimide dye by cross-oxidation by means of a cross-oxidizing photographic silver halide developing agent; said process comprising the steps:

(A) developing a silver image in said photographic element by means of an alkaline, photographic silver halide developer in the absence of a cross-oxidizing, photographic silver halide developing agent;

(B) fogging the resulting element;

(C) producing a dye image in the photographic element by means of an alkaline, cross-oxidizing, photographic silver halide developer; and (D) bleaching and fixing the photographic element by means of a silver halide bleaching and fixing solution; to produce a positive dye image in the photographic element.

35. A process as in claim 34 wherein said fogging is performed by means of a uniform flash exposure.

36. A process as in claim 34 wherein said photographic element after step (A) and before step (B) is treated by means of a photographic development stop bath.

37. A process as in claim 34 of producing a positive dye image in an imagewise exposed photographic element comprising a support having thereon, in reactive association, in binder, (a) photosensitive silver halide, and (b) a color-forming 4-(4'-secondary or tertiary-amino)anilino-1-carboxamidonaphthalene dye precursor consisting essentially of a compound represented by the formula:

said process comprising the steps:

(A) developing said photographic element in an alkaline, photographic developer in the absence of a cross-oxidizing, photographic silver halide developing agent;

(B) treating the photographic element by means of a photographic development stop bath;

(C) fogging the resulting element;

(D) producing a dye image in the photographic element by means of an alkaline, cross-oxidizing, photographic silver halide developer comprising an alkaline solution of 4-methyl-4-hydroxymethyl-1-phenyl-3-pyrazolidone; and then (E) bleaching and fixing the photographic element in a silver halide bleaching and fixing solution.

38. A process as in claim 34 of producing a positive dye image in an imagewise exposed photographic element comprising a support having thereon, in reactive association, in binder, (a) photosensitive silver halide, and (b) a color-forming 4-(4'-secondary or tertiary-amino)anilino-1-carboxamidonaphthalene dye precursor consisting essentially of a compound represented by the formula:

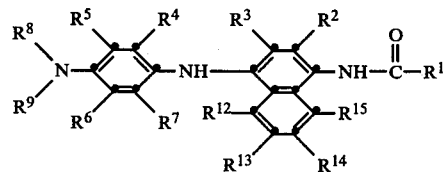

wherein:

$R^1$ is alkyl containing 1 to 25 carbon atoms, cycloalkyl containing 5 to 8 carbon atoms, aryl containing 6 to 25 carbon atoms, alkoxy containing 1 to 25 carbon atoms, aryloxy containing 6 to 25 carbon atoms,

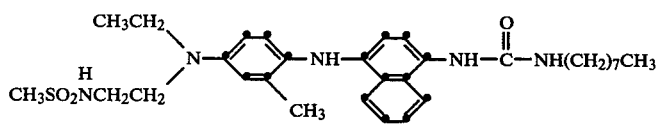

or a 5 or 6 member heterocyclic group;

$R^2$, $R^3$, $R^4$, $R^5$, $R^6$, and $R^7$ are individually hydrogen, alkyl containing 1 to 25 carbon atoms, aryl containing 6 to 25 carbon atoms, alkoxy containing 1 to 25 carbon atoms, arylsulfonyl containing 6 to 25 carbon atoms, chlorine, bromine, carbamoyl, sulfamoyl, carboxy, and carboxamido;

$R^8$ is hydrogen, alkyl containing 1 to 25 carbon atoms, aryl containing 6 to 25 carbon atoms, acyl containing 2 to 25 carbon atoms, or carbamoyl containing 2 to 25 carbon atoms;

$R^9$ is alkyl containing 1 to 25 carbon atoms, aryl containing 6 to 25 carbon atoms, acyl containing 2 to 25 carbon atoms, or carbamoyl;

$R^{10}$ and $R^{11}$ are individually hydrogen, alkyl containing 1 to 25 carbon atoms, aryl containing 6 to 25 carbon atoms, a carbocyclic group containing 6 to 8 carbon atoms, or taken together represent the atoms necessary to complete a 5 or 6 member heterocyclic ring;

$R^{12}$, $R^{13}$, $R^{14}$, and $R^{15}$ are individually hydrogen, alkyl containing 1 to 25 carbon atoms, cyano, sulfamoyl, chlorine, carboxamido, sulfonamido, bromine and alkoxy containing 1 to 25 carbon atoms;

said process comprising:

(A) developing said photographic element in an alkaline, cross-oxidizing, photographic silver halide developer composition to produce a negative dye image and silver image; then (B) removing at least part of the silver image from the photographic element.

41. A process as in claim 39 of producing a negative dye image in an exposed photographic element comprising a support having thereon, in reactive association, in binder, photographic silver halide and a color-forming dye precursor represented by the formula:

said process comprising the steps:

(A) developing said photographic element in an alkaline, photographic developer in the absence of a cross-oxidizing, photographic silver halide developing agent;

(B) treating the photographic element by means of a photographic development stop bath;

(C) fogging the resulting element;

(D) producing a dye image in the photographic element by means of an alkaline, cross-oxidizing, photographic silver halide developer comprising an alkaline solution of 4-methyl-4-hydroxymethyl-1-phenyl-3-pyrazolidone; and then (E) bleaching and fixing the photographic element in a silver halide bleaching and fixing solution.

39. A process of producing a negative dye image in an exposed photographic element comprising a support having thereon, in reactive association, in binder, photographic silver halide and a color-forming 4-(4'-secondary or tertiary-amino)anilino-1-carboxamidonaphthalene dye precursor which is converted upon processing of said element to a naphthoquinoneimide dye by cross-oxidation by means of a cross-oxidizing silver halide developing agent, said process comprising:

(A) developing said photographic element in an alkaline, cross-oxidizing, photographic silver halide developer composition to produce a negative dye image and silver image; then (B) removing at least part of the silver image from the photographic element.

40. A process of producing a negative dye image in an exposed photographic element comprising a support having thereon, in reactive association, in binder, photographic silver halide and a color-forming 4-(4'-secondary or tertiary-amino)anilino-1-caraboxamidonaphthalene represented by the formula:

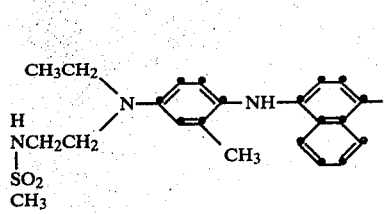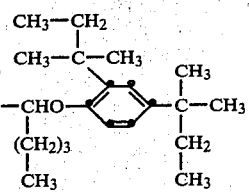

said process comprising:

(A) developing said photographic element in an alkaline, cross-oxidizing, photographic silver halide developer composition to produce a negative dye image and silver image; then (B) removing at least part of the silver image from the photographic element.

42. A process of producing a positive dye image and a positive silver image in an imagewise exposed photographic element comprising a support having thereon, in reactive association, in binder, (a) direct-positive photographic silver halide, and (b) a color-forming 4-(4'-secondary or tertiaryamino)-anilino-1-carboxamidonaphthalene dye precursor which is converted upon processing of said element to a naphthoquinoneimide dye by cross-oxidation by means of a cross-oxidizing silver halide developing agent, said process comprising:

(A) developing said photographic element in an alkaline, cross-oxidizing photographic silver halide developing composition; then (B) fixing the resulting photographic element to produce a positive dye image and a positive silver image.

43. A process as in claim 42 of producing a positive dye image and a positive silver image in an imagewise exposed photographic element comprising a support having thereon, in binder, (a) direct-positive photographic silver halide, and (b) a color-forming dye precursor represented by the formula:

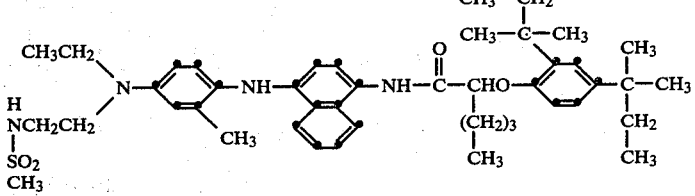

said precursor comprising:

(A) developing said photographic element in an alkaline, cross-oxidizing photographic silver halide developing composition; then (B) fixing the resulting photographic element to produce a positive dye image and a positive silver image.

44. A process as in claim 42 of producing a positive dye image and a positive silver image in an imagewise exposed photographic element comprising a support having thereon, in binder, (a) direct-positive photographic silver halide, and (b) a color-forming dye precursor represented by the formula:

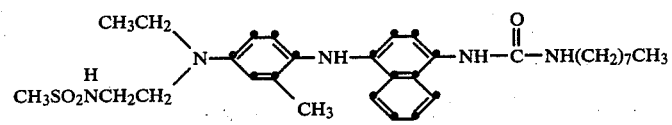

said process comprising:

(A) developing said photographic element in an alkaline, cross-oxidizing photographic silver halide developing composition; then (B) fixing the resulting photographic element to produce a positive dye image and a positive silver image.

45. In a photographic silver halide processing composition for producing a dye enhanced silver image comprising:

(a) a cross-oxidizing photographic silver halide developing agent, and (b) a color-forming dye precursor, the improvement comprising:

as said dye precursor, a 4-(4'-secondary or tertiaryamino)anilino-1-carboxamidonaphthalene color-forming dye precursor which forms a naphthoquinoneimide dye.

46. In a photographic silver halide processing composition for producing a dye enhanced silver image comprising:

(a) a cross-oxidizing photographic silver halide developing agent, and (b) a color-forming dye precursor, the improvement comprising:

as said dye precursor, a 4-(4'-secondary or tertiaryamino)anilino-1-carboxamidonaphthalene represented by the formula:

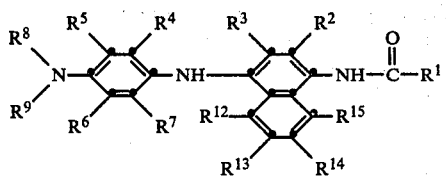

moyl, chlorine, carboxamido, sulfonamido, bromine and alkoxy containing 1 to 25 carbon atoms.

47. A photographic silver halide processing composition as in claim 45 wherein said dye precursor comprises a compound represented by the formula:

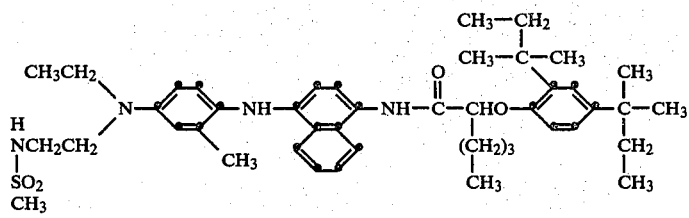

48. A photographic silver halide processing composition as in claim 45 wherein said dye precursor comprises a compound represented by the formula:

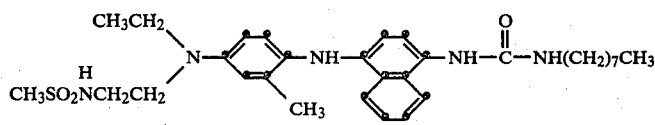

$R^1$ is alkyl containing 1 to 25 carbon atoms, cycloalkyl containing 5 to 8 carbon atoms, aryl containing 49. A photographic silver halide processing composition as in claim 45 wherein said dye precursor comprises a compound represented by the formula:

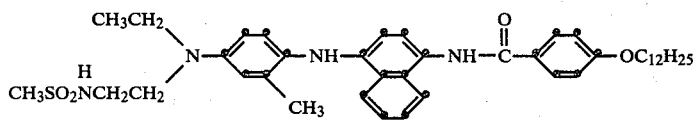

6 to 25 carbon atoms, alkoxy containing 1 to 25 carbon atoms, aryloxy containing 6 to 25 carbon atoms,

or a 5 or 6 member heterocyclic group;

$R^2$, $R^3$, $R^4$, $R^5$, $R^6$, and $R^7$ are individually hydrogen, alkyl containing 1 to 25 carbon atoms, aryl containing 6 to 25 carbon atoms, alkoxy containing 1 to 25 carbon atoms, arylsulfonyl containing 6 to 25 carbon atoms, chlorine, bromine, carbamoyl, sulfamoyl, carboxy, and carboxamido;

$R^8$ is hydrogen, alkyl containing 1 to 25 carbon atoms, aryl containing 6 to 25 carbon atoms, acyl containing 2 to 25 carbon atoms, or carbamoyl containing 2 to 25 carbon atoms;

$R^9$ is alkyl containing 1 to 25 carbon atoms, aryl containing 6 to 25 carbon atoms, acyl containing 2 to 25 carbon atoms, or carbamoyl;

$R^{10}$ and $R^{11}$ are individually hydrogen, alkyl containing 1 to 25 carbon atoms, aryl containing 6 to 25 carbon atoms, a carbocyclic group containing 6 to 8 carbon atoms, or taken together represent the atoms necessary to complete a 5 or 6 member heterocyclic ring;

$R^{12}$, $R^{13}$, $R^{14}$, and $R^{15}$ are individually hydrogen, alkyl containing 1 to 25 carbon atoms, cyano, sulfa- 50. A photographic silver halide processing composition as in claim 45 wherein said dye precursor comprises a compound represented by the formula:

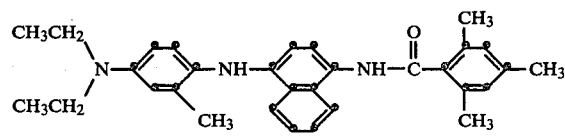

51. An exposed and processed photographic element comprising a support having thereon an image comprising a dye represented by the formula:

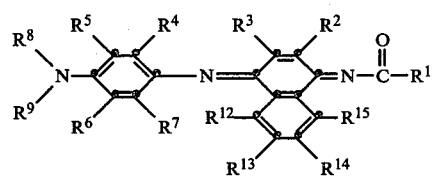

wherein:

$R^1$ is alkyl containing 1 to 25 carbon atoms, cycloalkyl containing 5 to 8 carbon atoms, aryl containing 6 to 25 carbon atoms, alkoxy containing 1 to 25 carbon atoms, aryloxy containing 6 to 25 carbon atoms,

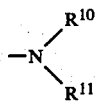

or a 5 or 6 member heterocyclic group;

$R^2$, $R^3$, $R^4$, $R^5$, $R^6$, and $R^7$ are individually hydrogen, alkyl containing 1 to 25 carbon atoms, aryl containing 6 to 25 carbon atoms, alkoxy containing 1 to 25 carbon atoms, arylsulfonyl containing 6 to 25 carbon atoms, chlorine, bromine, carbamoyl, sulfamoyl, carboxy, sulfonamido; and carboxamido;

$R^8$ is hydrogen, alkyl containing 1 to 25 carbon atoms, aryl containing 6 to 25 carbon atoms, acyl containing 2 to 25 carbon atoms, or carbamoyl containing 2 to 25 carbon atoms;

$R^9$ is alkyl containing 1 to 25 carbon atoms, aryl containing 6 to 25 carbon atoms, acyl containing 2 to 25 carbon atoms, or carbamoyl;

$R^{10}$ and $R^{11}$ are individually hydrogen, alkyl containing 1 to 25 carbon atoms, aryl containing 6 to 25 carbon atoms, a carbocyclic group containing 6 to 8 carbon atoms, or taken together represents the atoms necessary to complete a 5 or 6 member heterocyclic ring;

$R^{12}$, $R^{13}$, $R^{14}$, and $R^{15}$ are individually hydrogen, alkyl containing 1 to 25 carbon atoms, cyano, sulfamoyl, chlorine, carboxamido, sulfonamido, bromine and alkoxy containing 1 to 25 carbon atoms.

52. An exposed and processed photographic element as in claim 50 also comprising a binder.

53. An exposed and processed photographic element as in claim 50 also comprising a silver image.

54. An exposed and processed photographic element as in claim 51 comprising a support having thereon, in binder, an image comprising a dye represented by the formula:

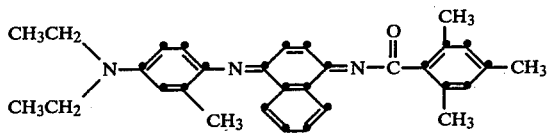

55. An exposed and processed photographic element as in claim 51 comprising a support having thereon, in binder, an image comprising a dye represented by the formula:

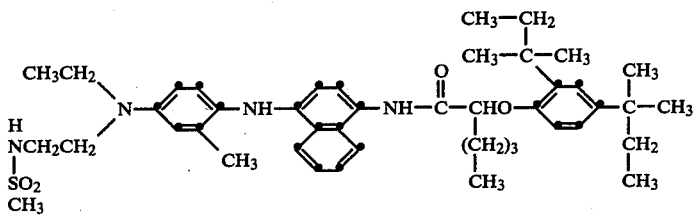

56. An exposed and processed photographic element as in claim 51 comprising a support having thereon an image comprising a dye represented by the formula:

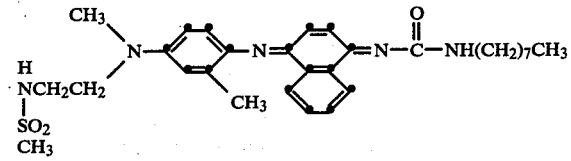

57. An exposed and processed photographic element as in claim 51 comprising a support having thereon an image comprising a dye represented by the formula:

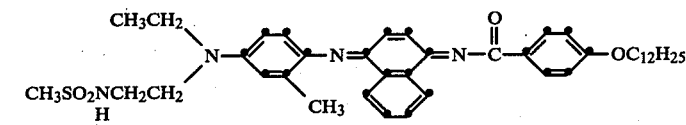

* * * * *

UNITED STATES PATENT AND TRADEMARK OFFICE
CERTIFICATE OF CORRECTION

PATENT NO. : 4,423,126
DATED : December 27, 1983
INVENTOR(S) : James E. Klijanowicz and Csaba A. Kovacs It is certified that error appears in the above-identified patent and that said Letters Patent are hereby corrected as shown below:

Columns 11-12, structure (35) should read (35)

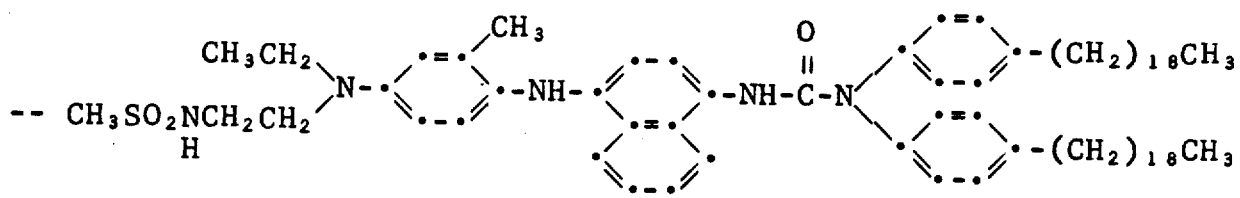

Columns 11-12, structure (37) should read (37)

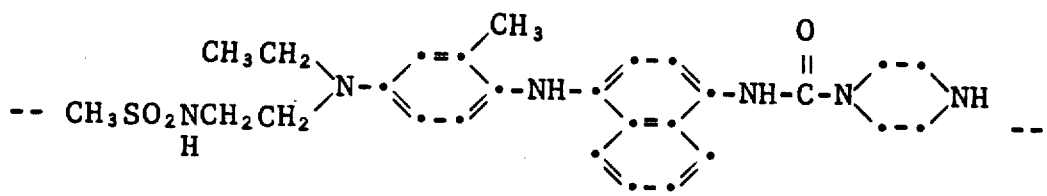

Column 18, lines 10-11, "3-pyrazolidione" should read
-- 3-pyrazolidone --;

UNITED STATES PATENT AND TRADEMARK OFFICE
CERTIFICATE OF CORRECTION

PATENT NO. : 4,423,126

DATED : December 27, 1983

INVENTOR(S) : James E. Klijanowicz and Csaba A. Kovacs

It is certified that error appears in the above-identified patent and that said Letters Patent are hereby corrected as shown below:

Column 56, lines 18-23, the formula should read

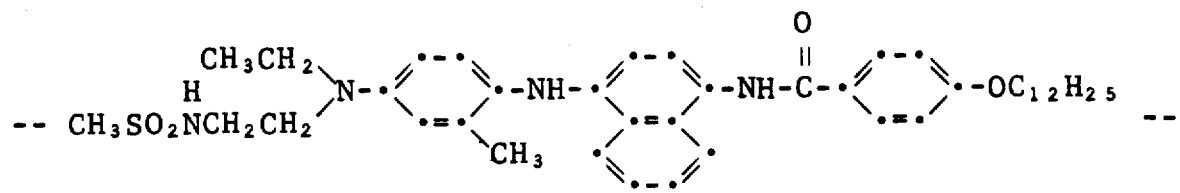

Signed and Sealed this

Eighth Day of May 1984

[SEAL]

Attest:

GERALD J. MOSSINGHOFF

Attesting Officer

Commissioner of Patents and Trademarks